(12) United States Patent
Kariniemi et al.

(10) Patent No.: US 9,895,243 B2
(45) Date of Patent: Feb. 20, 2018

(54) STENT HAVING ADJACENT ELEMENTS CONNECTED BY NARROW FLEXIBLE WEBS

(71) Applicant: W. L. Gore & Associates, Inc., Newark, DE (US)

(72) Inventors: Ryan D. Kariniemi, Flagstaff, AZ (US); Jeffrey J. Kustusch, Flagstaff, AZ (US); Mark J. Ulm, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 14/801,486

(22) Filed: Jul. 16, 2015

(65) Prior Publication Data

US 2016/0015538 A1    Jan. 21, 2016

Related U.S. Application Data

(60) Provisional application No. 62/025,670, filed on Jul. 17, 2014.

(51) Int. Cl.
*A61F 2/07* (2013.01)
*A61F 2/89* (2013.01)
(Continued)

(52) U.S. Cl.
CPC .................. *A61F 2/89* (2013.01); *A61F 2/07* (2013.01); *A61F 2/86* (2013.01); *A61F 2/915* (2013.01);
(Continued)

(58) Field of Classification Search
CPC .... A61F 2/89; A61F 2/07; A61F 2/844; A61F 2/86; A61F 2/915; A61F 2002/828;
(Continued)

(56) References Cited

U.S. PATENT DOCUMENTS 5,476,589 A    12/1995    Bacino
5,735,892 A    4/1998    Myers et al.
(Continued)

FOREIGN PATENT DOCUMENTS

EA    2 158 880    3/2010
EP    2 196 175    6/2010

OTHER PUBLICATIONS

International Search Report for PCT/US2015/040856 dated Mar. 1, 2016, corresponding to U.S. Appl. No. 14/801,486, 6 pages.
(Continued)

*Primary Examiner* — David Isabella
*Assistant Examiner* — Dinah Baria

(57) ABSTRACT

A stent incorporating flexible, preferably polymeric, connecting elements into the stent wherein these elements connect adjacent metallic stent element(s) across an intervening space and have optimized geometries. In one configuration the metallic elements are the result of forming the stent from a helically wound serpentine wire having intervening spaces between adjacent helical windings of the wire. The polymeric connecting elements are designed to fold within the space between the outer diameter of the stent and the inner diameter of the stent when the stent is subjected to compaction or bending. Other stent forms such as multiple, individual spaced-apart ring-shaped or interconnected stent elements may also be used.

38 Claims, 32 Drawing Sheets

(51) Int. Cl.
*A61F 2/86* (2013.01)
*A61F 2/915* (2013.01)
*A61F 2/82* (2013.01)

(52) U.S. Cl.
CPC .................. *A61F 2002/828* (2013.01); *A61F 2002/91558* (2013.01); *A61F 2210/0066* (2013.01); *A61F 2210/0076* (2013.01); *A61F 2220/005* (2013.01); *A61F 2230/0069* (2013.01); *A61F 2240/001* (2013.01); *A61F 2250/002* (2013.01); *A61F 2250/0018* (2013.01); *A61F 2250/0029* (2013.01); *A61F 2250/0068* (2013.01)

(58) Field of Classification Search
CPC ........ A61F 2250/0068; A61F 2250/002; A61F 2210/0076
See application file for complete search history.

(56) References Cited

U.S. PATENT DOCUMENTS

| | | | |
|---|---|---|---|
| 5,824,049 A | 10/1998 | Ragheb et al. | |
| 5,922,021 A * | 7/1999 | Jang | A61F 2/91 623/1.15 |
| 6,159,565 A | 12/2000 | Campbell et al. | |
| 6,224,627 B1 | 5/2001 | Armstrong et al. | |
| 6,299,604 B1 | 10/2001 | Ragheb et al. | |
| 6,322,847 B1 | 11/2001 | Zhong et al. | |
| 6,364,903 B2 | 4/2002 | Tseng et al. | |
| 6,858,221 B2 | 2/2005 | Sirhan et al. | |
| 7,049,380 B1 | 5/2006 | Chang et al. | |
| 7,306,729 B2 | 12/2007 | Bacino et al. | |
| 9,089,446 B2 | 7/2015 | Li | |
| 2001/0027339 A1 | 10/2001 | Boatman et al. | |
| 2005/0288769 A1 | 12/2005 | Globerman | |
| 2006/0020322 A1 | 1/2006 | Leynov et al. | |
| 2006/0122684 A1 | 6/2006 | Lye et al. | |
| 2006/0190072 A1* | 8/2006 | Das | A61F 2/91 623/1.15 |
| 2007/0038291 A1 | 2/2007 | Case et al. | |
| 2007/0219613 A1 | 9/2007 | Kao et al. | |
| 2009/0182413 A1 | 7/2009 | Burkart et al. | |
| 2010/0070024 A1 | 3/2010 | Venturelli et al. | |
| 2010/0324658 A1 | 12/2010 | Bogert | |
| 2011/0066227 A1* | 3/2011 | Meyer | A61F 2/90 623/1.42 |
| 2012/0109283 A1 | 5/2012 | Burkart et al. | |
| 2012/0232645 A1 | 9/2012 | Machold et al. | |

OTHER PUBLICATIONS

Annex to Form PCT/ISA/206 Communication Relating to the Results of the Partial International Search for PCT/US2015/040856 dated Oct. 19, 2015, corresponding to U.S. Appl. No. 14/801,486, 2 pages.

* cited by examiner

SECTION B-B

SECTION C-C

SECTION D-D

STENT HAVING ADJACENT ELEMENTS CONNECTED BY NARROW FLEXIBLE WEBS

FIELD OF THE INVENTION

The present invention relates to the field of implantable stents having flexibly connected adjacent structural elements.

BACKGROUND OF THE INVENTION

The use of implantable stents in the vasculature and other body conduits has become commonplace since first proposed by Dotter in the 1960s. These devices are required to have a small, compacted diameter for insertion into an intended body conduit and transport, typically via a catheter, to a desired site for deployment, at which site they are expanded to a larger diameter as necessary to fit interferably with luminal surface of the body conduit. Balloon expandable stents are expanded by plastically deforming the device with an inflatable balloon on which the expandable stent was previously mounted in the compacted state, the balloon being attached to the distal end of the catheter and inflated via the catheter. Self-expanding stents are forcibly compacted to a small diameter and restrained at that diameter by a constraining sleeve or other means. Following delivery to a desired site for deployment, they are released from the restraint and spring open to contact the luminal surface of the body conduit. These devices are typically made from nitinol metal alloys and typically rely on the super elastic and biocompatible character of the metal. Nitinol stents that rely on the shape memory attributes of that material are also known.

The evolution of implantable stents has also included the use of a tubular covering fitted to the stent, either to the outer surface, the luminal surface or to both surfaces of the stent. These covered stents have generally come to be referred to as stent-grafts. The coverings are generally of a polymeric biocompatible material such as polyethylene terephthalate (PET) or polytetrafluoroethylene (PTFE).

It is also known that stent graft coverings may be optionally provided with perforations if desired for particular applications. Because of the open area provided by the perforations, such devices having perforated coverings may be considered to be a sort of hybrid stent and stent-graft, as are devices that include stent frames having metallic stent elements or structure and polymeric elements connecting, covering or other otherwise being attached to the stent elements. The presence of the polymeric elements reduces the otherwise open space between the adjacent metallic stent elements, either very slightly or very substantially depending on the intended application and mechanical design.

Generally, a fully covered stent-graft can be considered to have a surface area (hereinafter $A_{max}$) equal to the outer circumference of the expanded stent multiplied by the length of the stent. For a conventional, open frame stent (as opposed to a stent-graft), the surface area represented by all of the stent elements is only a small portion of the maximum surface area $A_{max}$. The actual surface area covered by the stent, meaning the area covered by all components of the stent (including flexible connecting elements and graft covering material) in their deployed state, is $A_{stent}$. The porosity index, or P.I., describes the open area (the portion of the maximum surface area not covered by all components of the stent assembly) as a percentage of maximum surface area, wherein:

$$P.I. = (1 - (A_{stent}/A_{max})) \times 100\%.$$

One method of measuring the actual surface area covered by the stent ($A_{stent}$), involves the use of a machine provided by Visicon Inspection Technologies, LLC (Napa, Calif.). The Visicon Finescan™ Stent Inspection System (Visicon Finescan machine model 85) uses a 6000 pixel line scan camera to generate a flat, unrolled view of a stent. The Visicon Finescan also has an updated model, the Visicon Finescan Sierra that exists and may be used alternatively to measure actual surface area. In operation, the stent is mounted on a sapphire mandrel with a fine diffuse surface. This mandrel is held under the linear array camera and rotated by the system electronics and is used to trigger the linear array camera to collect a line of image data in a precise line-by-line manner. After a complete revolution an entire image of the stent is acquired. When the entire stent has been imaged, the software differentiates between the stent with cover and the background. The total number of picture elements (pixels) is compared to the total number of pixels associated with the stent and cover to determine Astent. Basic settings on the machine used for this type of determination are (for example): light, 100%; exposure, 0.3 ms/line; gain, 5; threshold, 50; noise filter, 20; smoothing, 4.

The open area may be a continuous single space, such as the space between windings of a single helically wound stent element. Likewise the open area may be represented by the space between multiple individual annular or ring-shaped stent elements. The open area may also be represented by the total area of multiple apertures provided by either a single stent element or by multiple stent elements providing multiple apertures. If multiple apertures are provided they may be of equal or unequal sizes. The use of a perforated graft covering or of polymeric elements in addition to metallic stent elements may also reduce the open area.

Stents having a porosity index of greater than 50% are considered to be substantially open stents.

In addition to the porosity index, the size of any aperture providing the open area must be considered if it is intended to cover only a portion of a stent area for a specific stent application. For multiple apertures, often the consideration must be for the largest size of any individual aperture, particularly if the apertures are to provide for a "filtering" effect whereby they control or limit the passage of biologic materials from the luminal wall into the flow space of the body conduit.

A shortcoming of some stent devices that combine metallic stent elements with flexible polymeric connecting elements is that the non-metallic elements, (e.g., polymer webs), when constrained circumferentially or axially or when bent into a curved shape, may protrude into the luminal space of the device. This type of protrusion into the luminal space of the device may create opportunities for clinical complications such as stenosis, thrombus, altered blood hemodynamics, and associated complications.

In light of the foregoing, there is an ongoing need for endoprostheses such as stents or stent grafts that when deployed have sufficient radial force, porosity, and flexibility, while having minimal impact to blood hemodynamics and other clinical complications typically associated with interfering structures of a medical device. The embodiments described herein provide a flexible endoprosthesis (e.g. a stent or stent graft) with potentially less interference into the luminal space than currently known devices.

SUMMARY OF THE INVENTION

An endoprosthesis is described having a length, a radius, an inner circumference and an outer circumference, the endoprosthesis comprising adjacent stent elements having spaces there between, the adjacent stent elements including multiple apices with multiple flexible connecting elements that extend across the spaces between the adjacent stent elements, wherein the flexible connecting elements are biased to fold substantially between the inner circumference and the outer circumference when the endoprosthesis is compacted. Folding of the flexible connecting elements is the result of the application of a longitudinal (axial) or alternatively a bending force applied to the endoprosthesis. The phrase "folded flexible connecting elements" thus describes the bent shape of the flexible connecting elements resulting from the application of such forces. Prior to the application of such forces, the flexible connecting elements are typically substantially straight between their attachment points to the stent structure The flexible non-metallic connecting elements or measured webs with an average width to thickness ratio of less than 10 (as transversely at the middle of the length of the web) provide a stent with flexibility, useful resistance to forces that may be applied to the device in vivo such as torsion forces, bending forces, axial tension or compression, or radial compression, and minimize encroachment of portions of the device into the luminal or abluminal space.

Another embodiment provides an endoprosthesis having a length, a radius, and a circumference, the endoprosthesis comprising adjacent stent elements having a space there between, the adjacent stent elements including multiple apices wherein one apex of a stent element is connected across the space to a pair of apices on the adjacent stent element wherein the flexible connecting element has a section modulus $M_r$ in a direction aligned with the radius of the endoprosthesis (i.e. as measured along an imaginary line extending perpendicularly through a longitudinal axis of a substantially tubular device) and a section modulus $M_p$ aligned in a direction perpendicular to $M_r$ of the endoprosthesis (i.e. in a direction tangential to a circumference of a substantially tubular device); and wherein $M_r/M_p > 0.2$.

In one embodiment the endoprosthesis may be fabricated from a length of serpentine, helically wound wire wherein the helically wound wire provides the general cylindrical form of the endoprosthesis and wherein the serpentine form of the wire provides sequential apices along the length of the wire with each sequential apex pointing towards alternate ends of the endoprosthesis. It is noteworthy that while the endoprosthesis may be fabricated from a single length of helically wound serpentine wire, the adjacent windings of the helically wound wire constitute the adjacent stent elements with spaces there between as referred to above. Helically wound stent frames are inherently unstable in absence of a secondary linkage, such as a flexible connecting element, connecting adjacent stent elements across intervening spaces. Utilization of the described flexible connecting element to interconnect adjacent rows stabilizes the helical structure and limits axial elongation, torsion and bending while allowing a high degree of flexibility.

Other stent forms such as multiple, individual spaced-apart ring-shaped stent elements may also be used. Ring shaped stent elements may be in the form of zig-zag elements creating a circumferential ring, or interconnected elements that provide diamond shaped openings in a circumferential sequence when the device is diametrically expanded. Alternatively, embodiments presented that utilize the helically wound serpentine forms are preferred for many applications. The stent is preferably self-expanding (made from materials such as nitinol) but may also be made from materials suitable for balloon expandable stents (e.g., stainless steel, magnesium based alloys, magnesium, cobalt chromium alloy, titanium or titanium based alloys). The stent may also be configured such that polymeric linkages may connect metallic structure(s) circumferentially and/or longitudinally.

In addition to stents and stent-grafts, embodiments of the endoprosthesis described herein may be manufactured in suitable forms to serve as other diametrically expandable implantable articles for use in various bodily conduits. These may include embolic filters, various vascular occluders, vena cava filters, heart valve stents, etc.

Flexible connecting elements inherently provide flexibility to the endoprosthesis but also may have a tendency to fold into the lumen when compacted (e.g. circumferentially, diametrically, axially, longitudinally, bending etc.). This folding of the flexible connecting elements into the lumen (when the endoprosthesis is constrained circumferentially or axially or when bent into a curved shape) can have undesirable clinical responses. Manufacture of the flexible connecting elements as described herein can reduce the amount of folding of the flexible connecting elements into the lumen and therefore aid in a more desirable clinical outcome.

The adjacent, spaced-apart stent elements are circumferentially or helically oriented, meaning that they have a general direction of orientation perpendicular to the longitudinal axis of the stent, when the stent is in a straight, unbent state.

A method of making involves the application of a biocompatible polymeric covering to the chosen stent form to create, temporarily, a stent-graft. The covering is preferably of a strong and thin material and may be in a tubular form, although sheet forms (e.g., relatively wide films cut into narrow tapes, or wide films applied such that there is a seam line running longitudinally along the length of the endoprosthesis) are preferred for manufacturing as will be described. The covering can be applied to the outer surface of the stent, but may also be applied only to a luminal surface, or alternatively may be applied to both the luminal and abluminal (outer) surfaces of the stent. A covering is applied so that a desired thickness of a flexible connecting element can be achieved. The thickness of the flexible connecting element compared to the width of the flexible connecting element aids in the folding of the flexible connecting element (when the endoprosthesis is constrained circumferentially or axially or when bent into a curved shape) to be substantially within the outer and inner circumference of the metallic structure. Covering both the luminal and abluminal surfaces allows for the possibility of covering substantially all of the metallic surfaces of the stent with the desired polymer. The polymeric film covering in some embodiments comprises a thermoplastic film with strength properties that result in relatively uniform directional shrinking properties when the film is subjected to heat above its melt point. The film-covered stent graft may be provided with shaped apertures or partial apertures (slits or other puncture openings) through all or most of the thickness of the film, such as at locations between adjacent stent elements, as will be further described. The punctured stent-graft is then exposed to heat above the melt temperature of the film which causes the film to shrink back from the edges of the previously created puncture, resulting in openings through the wall of the stent. These openings are of size, shape, quantity and orientation that are a result of the size, shape, quantity and orientation of the previously created punctures, the amount of heat subsequently applied and the thickness and type of polymeric film used. It is apparent that these are manufacturing variables that may be controlled as desired. The resulting open area of the stent (i.e., porosity index) may cover a wide range but typically will be greater than 50% and for example may be around 70% to 80%. The remaining polymeric film following the heating step is in the form of polymeric webs extending across the space between adjacent stent elements, these polymeric webs thereby serving as flexible connecting elements between the adjacent stent elements.

In various embodiments, the width and thickness of the flexible connecting element can be controlled. For example, the amount of film applied, (i.e., thickness), and/or the size of the slits or apertures, and/or laser settings, and/or by layering films having different heat retraction properties. For example, if two films having different heat retraction properties are layered together, and then slit and heat retracted, a transverse cross section of the resulting flexible connecting element may have a variable width through its thickness.

Further, the finished open frame stent may optionally be provided with another, additional covering of polymeric graft material to create a stent-graft if desired. This graft covering is easily adhered or bonded to the covering or coating that is provided over the stent elements (e.g., the wire) and forms the flexible interconnecting webs. This covering may have different material properties that aid in strength or adhesion or carrying therapeutic agents. The cover may further then be punctured to create a stent graft that has an axially strong linkage in contact with another layer of material that may provide as a carrier for a therapeutic agent.

The polymeric covering of these finished devices (that include a multiplicity of openings and a multiplicity of flexible polymeric interconnecting webs) is generally continuous or substantially continuous between the stent ends, being the result of having been made from a continuous sheet of film or the result using helically wrapped polymeric tape with overlapping adjacent edges that are melt-bonded together. The film covering that forms these continuous webs is well adhered to the stent elements.

In another embodiment, the polymeric covering is perforated along the metallic structure portion such that the metallic portion and the polymeric covering would be exposed to the lumen wall. This allows the stent graft with the polymeric covering to have metallic anchoring to the vessel wall. The area of the stent that has the polymeric material removed can be used as a reservoir for therapeutic agents. This removal process can be done with a laser. These reservoirs can then have another layer of material spanning over the reservoir to create an enclosed or partially enclosed pocket or a protective layer for the therapeutic agent. The vessels of the body typically adhere well to metallic components, so by providing openings along the metallic frame (i.e. polymeric material is removed) the stent graft has anchor points where the body can adhere the stent to the vessel. In addition, these openings can act as anchor points along the stent and provide stop points for a deployment system such as a deployment system described in U.S. Pat. No. 6,224,627 to Armstrong et al. that may allow for a more controlled deployment.

In another embodiment, the section modulus ($M_r$) may vary along a length of the flexible connecting element spanning an opening between adjacent stent elements. The varying section modulus ($M_r$) can provide reservoirs for therapeutic agents. The varying section modulus can also provide for "stop points" (i.e. a discontinuity in the flexible connecting element located at selected positions along the length of the stent structure (e.g. the wire)) These stop points may provide for a more controlled deployment by creating a location that a constraining covering can rest or stop against during a deployment.

In an another embodiment, a flexible connecting element (i.e., "linkage") may be further tailored to optimize side branch and main branch luminal hemodynamics. The hemodynamics may be improved by tailoring of the linkage cross sectional geometry. For example, a 0.003 inch (0.0762 mm) thick linkage has a lower volume of a stagnation zone (e.g blood entering into or exiting from a side branch of the major stented vessel, or simply the character of the blood flow immediately adjacent to the luminal surface of the endoprosthesis) than a 0.002 inch (0.0508 mm) thick linkage, but a more optimized linkage thickness may be in the range of 0.005 inch (0.127 mm) and 0.010 inch (0.254 mm). Also, a narrower linkage may improve hemodynamics compared to a wider linkage. For example, a 0.020 inch (0.508 mm) wide linkage may be more optimized than a 0.100 inch (2.54 mm) wide linkage in relation to improved hemodynamics. The hemodynamics can also be tailored by profiling or shaping of the cross section of the linkage. The linkage can have a cross section that is of varying shapes. These cross sections can be achieved by covering the stent in films that have different heat retraction rates. They can also be tailored by other means such as a laser. A linkage cross section can be shaped to deflect flow to a desired location. For example, in the venous system, a linkage may be profiled to deflect flow from a side branch into the main branch.

In another embodiment, a flexible connecting element may be tailored to create stagnation zones or to limit the amount of flow that passes by the linkage. One example of this use is if the device is to be used to exclude an aneurysm, the cross section is designed to create a stagnation zone in the appropriate region of the aneurysm (e.g to decrease aneurysm coagulation time).

In another embodiment, a flexible connecting element or linkage may be created by using a material that has elastic properties. When the linkage is made from a material that has elastic properties, a device can have longitudinal and circumferential expansion. This may prove to be advantageous in a tortuous anatomy where the material or covering or linkage can go into longitudinal tension on one side of a curved portion and longitudinal compression on another side of a curved portion, e.g. an opposite side. Another potential advantage is if the device has a clot or thrombus attached to it, the device can be circumferentially dilated, by a balloon for example, to dislodge a clot or thrombus. If balloon dilation is relaxed the device can go back to its pre-dilated diameter. A method of applying an elastic material to a stent is to apply the material in a stretched configuration up to the point of plastic deformation.

In another embodiment, a connecting element may be made of a material that has elastic and non-elastic properties. For example, an elastic material may be laid adjacent or on top of a non-elastic material or a non-elastic material may be laid adjacent or on top of an elastic material. The materials may also be alternating through the thickness of a linkage. One potential advantage to using elastic materials and non-elastic materials on the same device is that it may be possible to achieve a longitudinally stiff device in tension (and when compressed longitudinally the elastic portion folds substantially "in plane") and an elastic device circumferentially.

In another embodiment, a linkage can have a reinforcement member created to make a device more stiff when the device is constrained in diameter. Typically, the stiffness of a device is controlled by a metallic structure of the device. For example, a wire diameter of the device can be changed to change the amount of radial stiffness and it can be tailored to a desired state. In present known devices, the larger the wire diameter, the stiffer the device. In some cases, a stiffer device has a tradeoff of less fatigue resistance. One way to combat this tradeoff, is to add a reinforcement feature to the linkage. This reinforcement feature may be metallic or non-metallic. It can be layered into the film when the films are being applied or applied after heat treatment of the polymer films. The reinforcement feature may also be made by creating a densified region or a region that is stiffer than the polymer web.

In another embodiment, a linkage may have an ingrowth layer applied to it. An ingrowth layer meaning a layer that allows ingrowth of the vessel into the polymer covering. The ingrowth layer may be added after the linkages have been created or it may be incorporated into the layering of the films. The ingrowth layer may be embedded in the layers and then exposed through a subsequent laser or other removal process.

Linkages that span the space between adjacent stent elements may take on various shapes and sizes. The linkage may have an undulating pattern that aids in the linkage folding substantially "in plane" and in some cases within the space between the outer and inner boundary of the metallic portion of the device.

Still further, these devices and linkages may be provided with coatings (e.g., elutable coatings) of various therapeutic agents (e.g., heparin) by various means known in the art that are suitable to the particular agent. Furthermore, these devices may be applied with hydrogels that allow the linkages to change shape, e.g., by swelling. These hydrogels can be applied to the entire device or strategically to certain linkages by known methods in the art.

Stents made as described herein have good conformability enabled by the flexible interconnecting webs between adjacent stent elements that provide flexibility and anatomic apposition while increasing luminal space by potentially minimizing material folding into the lumen. In addition they may allow for optimized blood flow passing through the linkage. This optimization can be used to minimize stagnations in the main vessel and maximize stagnation in an aneurysm. Furthermore, they may enhance the linkages and may create better clinical outcomes. They also have good flexural durability enabled by interconnecting webs between adjacent stent elements that mitigates fracture due to cyclic longitudinal bending in curved anatomies. The expandable device is scalable to accommodate a range of vessel sizes (e.g. 3 mm-55 mm).

Potential clinical applications of the expandable device described herein include, but are not limited to: congenital defects (i.e., pulmonary artery stenosis, aortic coarctation), adjunctive aortic therapy (i.e., Type I endoleaks; aortic side branch stenting), peripheral artery disease (i.e., renal and iliac artery stenosis, aneurysm, and dissection) and venous applications.

"In plane" is defined in the context of when the stent is substantially fully longitudinally (i.e. axially) compacted using manually applied force. In one embodiment, a fully longitudinally compacted stent with flexible connecting linkages can be observed when an apex of one winding is closer to the apex of an adjacent winding than the apices 22b of the adjacent winding. Under these circumstances, the characteristics of the linkages being "in plane" is defined as the linkage orienting (e.g. folding) itself such that a substantial portion of the linkage length is within an outer circumference or boundary of one individual stent winding and inner circumference or boundary of the same individual stent winding.

"In plane" test method: Obtain a stent with flexible interconnecting webs between adjacent stent elements. Obtain a mandrel with an outer diameter approximately 2 mm smaller than the inner diameter of the stent. Insert the mandrel into the inner diameter of the stent so that the flexible interconnecting webs that are to be evaluated are outside of the mandrel. Longitudinally compress the stent by up to the stent's maximum longitudinal compression so the flexible interconnecting webs are substantially limiting further longitudinal compression of the stent (e.g. see FIG. 8A). Visually evaluate the flexible interconnecting webs to determine if the straight portion of the web is not significantly folded and if the web is substantially within the outer boundary and inner boundary of an individual stent winding that a given web is attached to.

DETAILED DESCRIPTION OF THE DRAWINGS

Figure 1A:
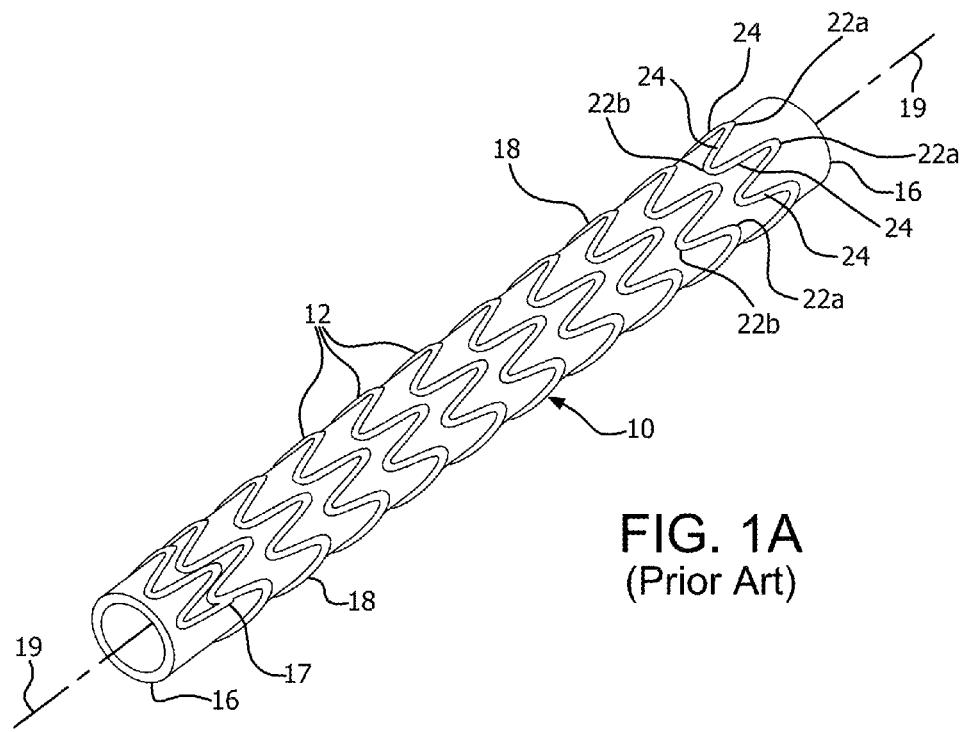
FIGS. 1A and 1B describe respectively a perspective view and a plan view of a helically wound serpentine wire form (previously known) of a stent as described herein.

As generally described above, a variety of stent forms may be usefully provided including the flexible connecting elements taught herein. FIG. 1A shows a perspective view of a stent 10 for use in various embodiments as described herein. The stent 10 shown comprises a helical winding of a length of serpentine wire 18. Sequential windings of the helical wound serpentine wire 18 result in spaced-apart adjacent stent elements 12. The ends 17 of wire 18 may be secured by any suitable method (e.g., welding) to the longitudinally adjacent helical winding. For clarity, stent 10 is shown with a mandrel 16 extending through and beyond both ends of the stent lumen, making the side closest to the viewer visually apparent while blocking the view of the side of stent 10 furthest from the viewer. Mandrel 16 is present only for clarity of visualization and is not a part of stent 10.

The helically wound serpentine wire 18 extends continuously between opposing ends of stent 10, wherein opposing apices 22a and 22b formed of wire bends of relatively small radii are interconnected by straight or relatively straight wire segments 24. The apices typically "point" in directions that are substantially parallel to the longitudinal axis 19 of the mandrel 16 and the tubular form of the stent 10, with alternating apices 22a and 22b pointing in opposite directions, that is, pointing to opposite ends of the stent. In the embodiments as shown by FIG. 1A, apices pointing in one direction (e.g., apices 22a) are aligned along a first common line while the apices pointing in the opposite direction (e.g., apices 22b) are aligned along a second common line that is parallel to the first common line.

Figure 1B:
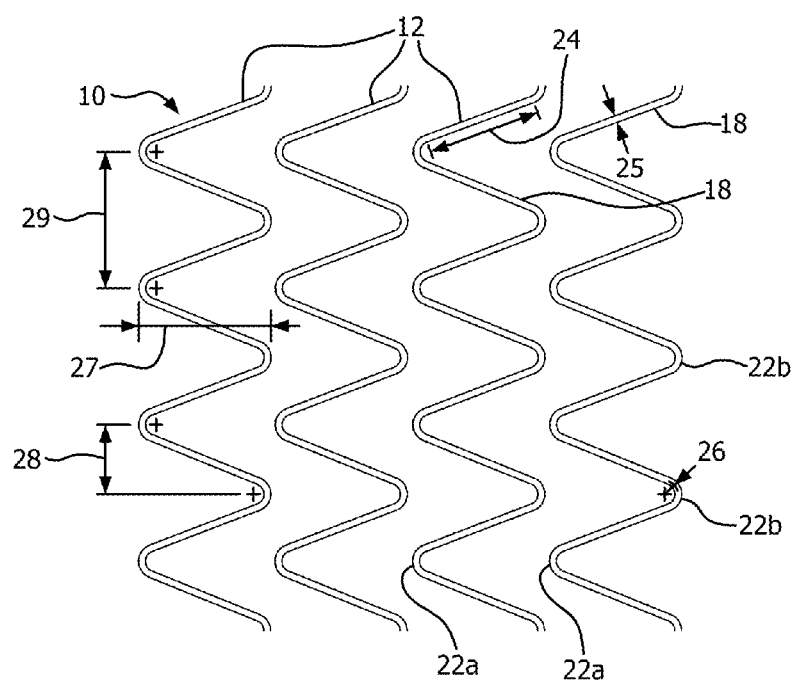

FIG. 1B shows a plan (or flattened) view of details of the serpentine wire form described by FIG. 1A; dimensions relate to the method of making described below. Dimension 27 is considered as the height (amplitude) of adjacent opposing apices while dimension 28 is the width of adjacent opposing apices. Dimension 29 describes one full period of the serpentine form. Wire diameter 25 and bend radius 26 of the apices 22 may be chosen as appropriate. Substantially triangular spaces are defined by a triangular boundary wherein two apices of the triangular space are a 22b apex and the other apex is a 22*a* apex that is longitudinally distal of the 22*b* apices. The 22*b* apices point proximal and the 22*a* apices point distal.

Figure 2A:
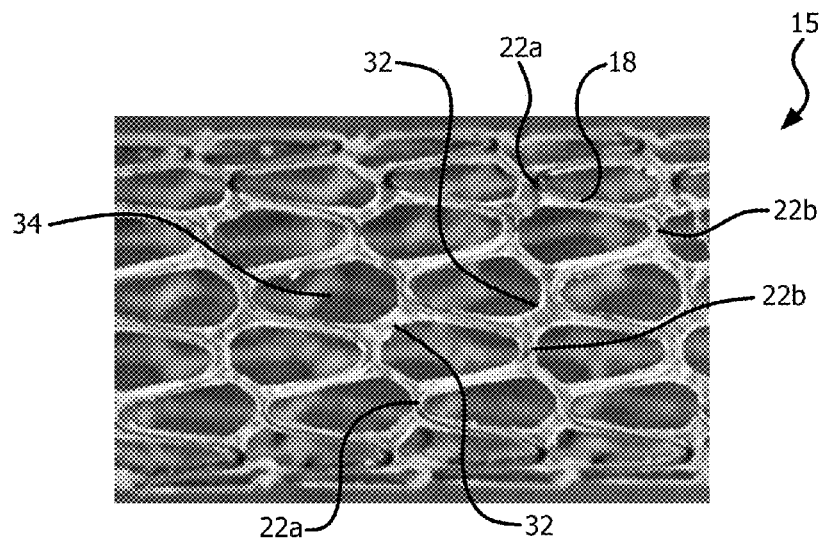
FIG. 2A is a photomicrographic side view of a portion of a helically wound serpentine wire stent (previously known) provided with flexible interconnecting webs between adjacent stent elements.
Figure 2B:
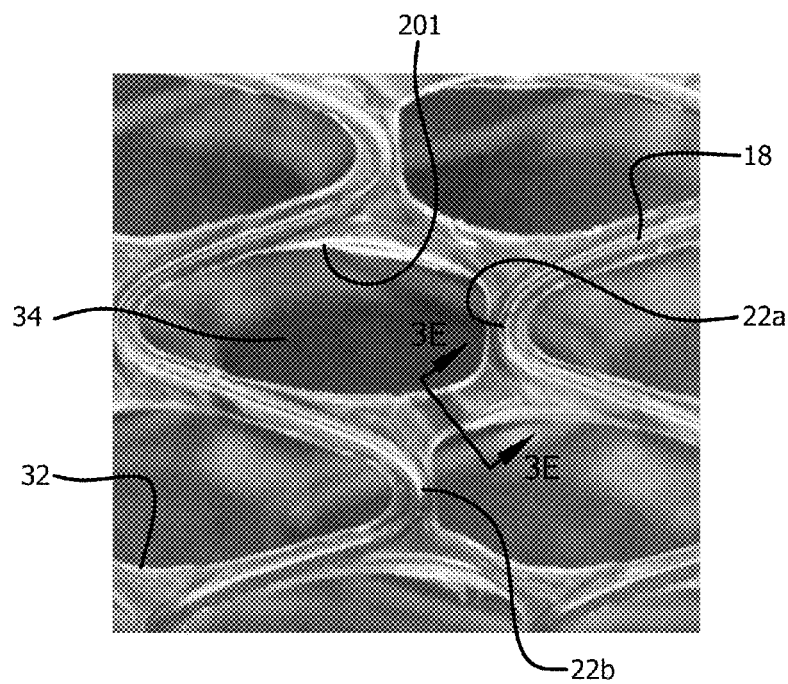
FIG. 2B is a further magnification of a portion of a similar helically wound serpentine wire stent in a relaxed or non-folded configuration (e.g. minimal longitudinal compression on the stent) provided with flexible interconnecting webs shown by FIG. 2A.

FIG. 2A is a side magnified photographic perspective image of previously known art, showing a portion of the length of an open-frame stent 10 wherein spaced-apart, adjacent stent elements 12 (e.g., two adjacent apices 22*a* connected to opposing apex 22*b*) are interconnected by a pair of flexible polymeric webs 32. Guitar pick shaped openings 34 are generally defined by the form of helically wound serpentine wire 18 and flexible polymeric webs 32. FIG. 2B is a magnified photographic perspective image of previously known art wherein the enclosed openings 34 are shown to be somewhat oval shaped. The openings are separated by a polymeric web 32 wherein the polymeric web 32 is made up of substantially only a shaped section 201.

In various embodiments, a finished stent 60 can be created. A covering can be applied and modified to create alternative flexible linkage elements 32. For example, as shown in the photomicrographic plan view of FIG. 2C and the schematic plan views of FIG. 2D, the polymeric covering may be formed into flexible linkage elements 32 associated with an arrowhead shaped opening 34. The opening 34 may be formed when the cover is modified (e.g. a slit or perforation and then optionally further heat retracted) to form the polymer webs 32. The opening 34 may have a first end at least partially bounded by an apex 22*a* (or 22*b*) and another end opposite the first end at least partially bounded by another apex 22*a* (or 22*b*). The opening 34 may be bound by five concave shaped sections (201, 216) and one convex shaped section 202 as viewed from within the opening 34. Four of the concave shaped sections 201 may be at least a portion of one of the webs 32 bounding the opening 34 and one of the concave shaped sections 216 may be an apex 22*a* or 22*b* or a vestigial edge 36 associated with an apex 22*a* or 22*b*. The convex shape 202 as viewed from within the opening 34 may be an apex 22*a* or 22*b* (opposite the apex 22*a* or 22*b* associated with the concave curved section 201) or associated with apex 22*a* or 22*b* (e.g. vestigial edge 36). The opening 34 may have a first end and a second end opposite the first end and one of the ends has a concave shape 216 and the other end has a convex shape 202 as viewed from within the opening 34. Alternatively, the opening 34 may have a first end and a second end opposite the first end and one of the ends has a concave shape 216 and the other end has a convex shape 202 and two concave shapes 201 as viewed from within the opening 34.

Figure 2C:
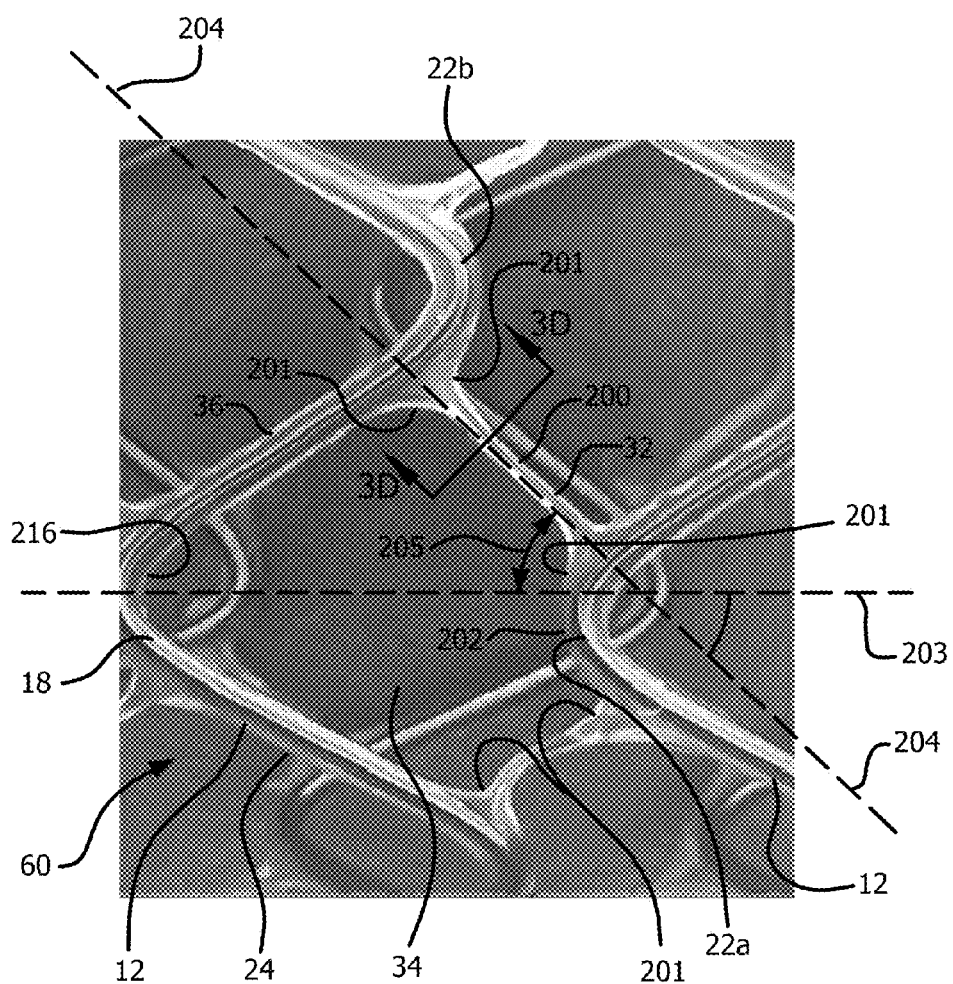
FIG. 2C is a perspective view of a stent in a relaxed or non-folded configuration (e.g. minimal longitudinal compression on the stent) in accordance with an embodiment described herein, wherein each single opening shown has an arrow head shape and the connecting flexible linkages are substantially non-curved.
Figure 2D:
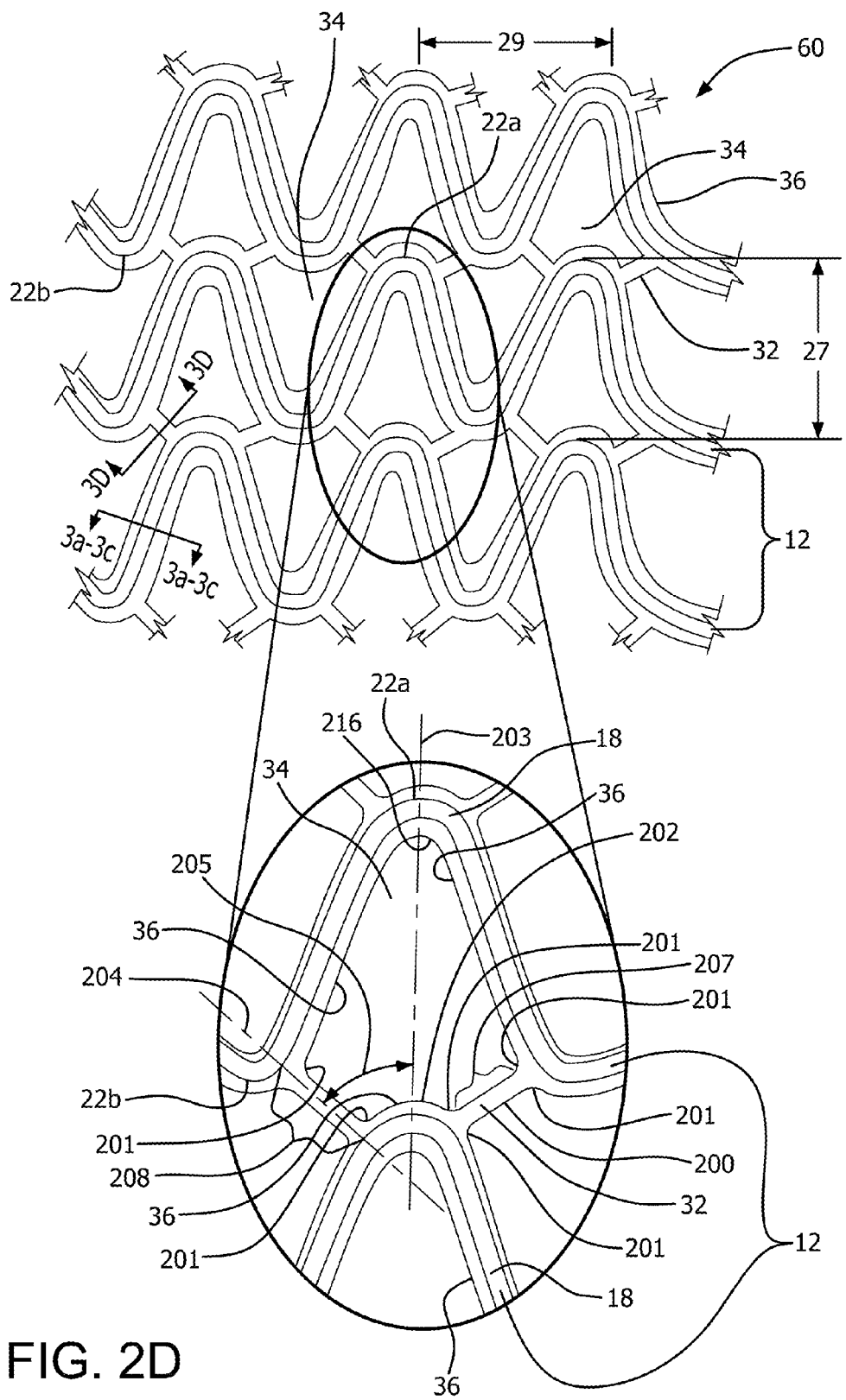
FIG. 2D is a plan view of a stent in accordance with an embodiment.

As shown in FIG. 2D, interconnecting elements 32 have a web centerline 204 through the center of the length of an individual, randomly selected web (i.e., extending between the adjacent wire apices joined by that web). The web centerline 204 may form an angle 205 of between 15 and 75 degrees with respect to a parallel line 203 with the web centerline 204 of the stent (or parallel with the centerline 19 of mandrel 16 shown in FIG. 1). Said otherwise, for this type of stent with elements interconnected by flexible webs 32, the webs 32 may be oriented at an angle to the length of the stent. The web centerline 204 can also be considered a line of symmetry for the polymer web 32 for the portion of the web 32 that spans the space between adjacent stent elements 12. The polymer web 32 has a web length 208. The web length 208 is the distance between wire 18 on one stent element 12 and wire 18 on an adjacent stent element 12 along the web centerline 204. In previously known stents, a web length 208 is approximately three times its width 300. According to one embodiment the web length 208 is at least 5 times its width 300 and in another embodiment the web length 208 is 10 times its width 300.

Figure 2E:
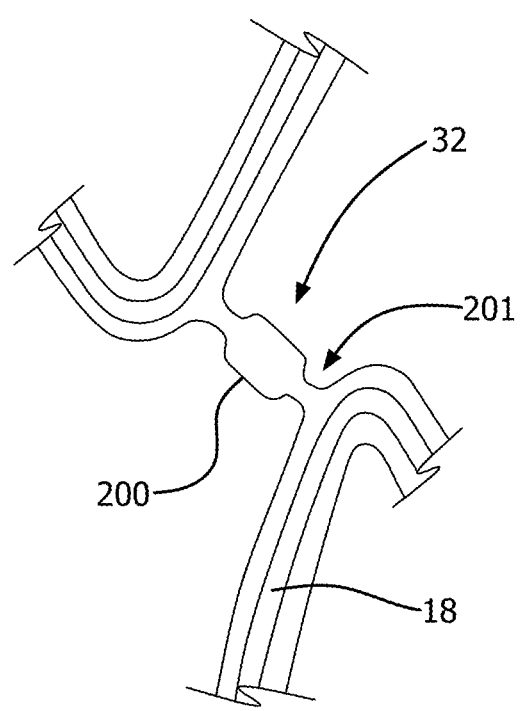
FIG. 2E is a plan view showing a configuration according to an alternative embodiment.

Furthermore, as shown in FIG. 2D, the web 32 has a straight section 200 and a curved section (or concave section as viewed from within opening 34) 201 and the curved sections merge tangentially into the stent element or a vestigial edge 36 along the stent element. The enlarged portion of FIG. 2D shows how these flexible polymeric webs 32 are generally straight until the web transitions from a straight section 200 to a curved section 201 and the curved section 201 is joined to and attached to stent element 12 (e.g. via the vestigial edge 36). The webs 32 are shown to have substantially straight sections 200, with a straight section length 207, and substantially curved sections 201 wherein the straight sections 200 span more of the distance across a space between adjacent stent elements 12 than the curved section 201. Curved sections 201 can be symmetrical about a centerline 204 or they can be unsymmetrical. The straight section 200 is narrower than the curved sections 201, but alternatively the straight section 200 may be wider than a curved section 201 as shown in FIG. 2E.

Figure 3A:
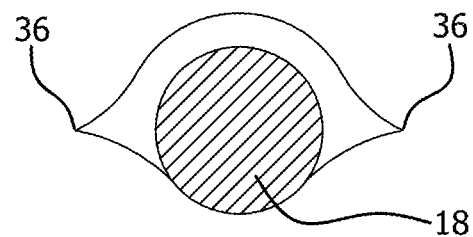
FIGS. 3A-3C are transverse cross sectional views of a helically wound serpentine wire in stent form with a covering applied to the helically wound serpentine wire.
Figure 3B:
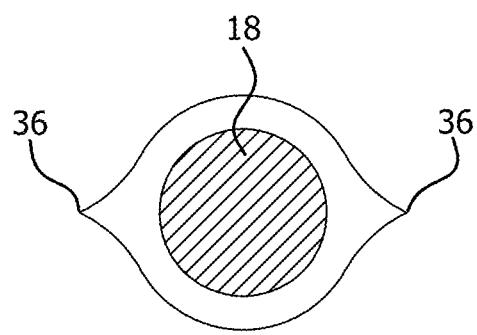
Figure 3C:
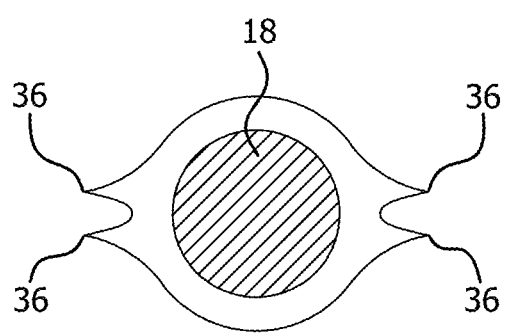

In various embodiments described by FIGS. 3A-3C, a stent has a transverse cross section across a wire 18. For example, a finished stent with a covering that has been applied, slit, and heat retracted can have a transverse cross section with a vestigial edge 36 when the covering has been applied to either the outer or inner surface of the stent as shown in FIG. 3A. The stent may have a transverse cross section with a covering on the inner and outer surfaces of the stent 60 and have vestigial edges 36 as shown in the embodiments described by FIG. 3B and FIG. 3C.

Figure 3D:
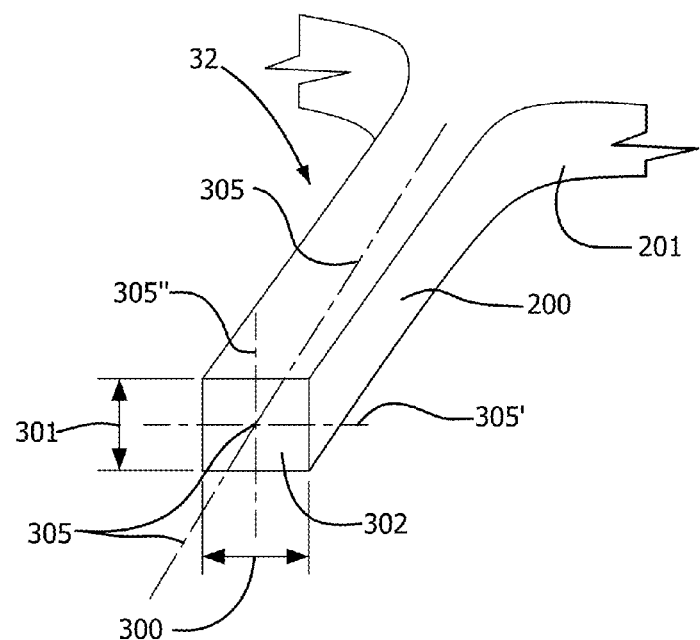
FIG. 3D is a representation of a perspective transverse cross section of a flexible connecting linkage with a $M_r/M_p$ ratio>0.2.

In various embodiments, a web 32 has a cross section 302 with an associated section modulus. For example, as shown in FIG. 3D, the polymeric web 32 from FIG. 2D, has a width 300 and a thickness 301 and an associated section modulus. The section modulus calculation for a rectangular cross section is calculated as $$SectionModulus = \frac{Moment\_of\_Inertia}{y}$$

where y is equal to the distance from the centroid of the cross section 302 to an outer edge. In the case of a rectangular cross section, the section modulus can be generally simplified to $$\frac{base\_x\_width^2}{6}.$$

In the radial direction the section modulus can then be calculated as, $$Mr = \frac{width(300) \times thickness(301)^2}{6}$$

and in the perpendicular direction the section modulus is calculated as $$Mp = \frac{thickness(301) \times width(300)^2}{6}.$$

The width 300 is the maximum distance of the cross section 302 of the web 32 in the perpendicular direction. The thickness 301 is the maximum distance of the web 32 in the radial (i.e. as measured along an imaginary line extending perpendicularly through a longitudinal axis of a substantially tubular device) direction of the section 302. Section 302 is in a direction perpendicular to the straight section 200. A transversely cut cross section 302 may be taken at the middle of the length of the web 32 in any suitable fashion whereby the dimensions of the web are not deformed by the sectioning (e.g cutting) process. The subsequent measurement of the dimensions of the transverse cross section 302 may be accomplished using conventional scanning electron microscopy machine.

In various embodiments, a web can have a $M_r/M_p$ ratio. For example, a web 32 may have a $M_r/M_p$ ratio>0.5, but can also have a $M_r/M_p$ ratio>0.2 and still fold substantially "in plane". The $M_r/M_p$ ratio that allows for in plane bending or folding can change as the web angle 205 of the polymer web changes. For example, as the web angle 205 as shown in FIG. 2D approaches zero degrees from a line 203 running longitudinally through apices 22a, the $M_r/M_p$ ratio may need to be closer to 1 in order to fold substantially in plane with a longitudinally compressed device. As the polymer web angle 205 approaches 90 degrees from the longitudinal line 203 through longitudinally adjacent apices 22a and a web center line 204, the $M_r/M_p$ ratio may also need to be closer to 1 for a circumferentially reduced device. The geometry of the web angle 205 can have an effect on what the $M_r/M_p$ ratio needs to be. In one embodiment, the polymer web angle 205 is oriented at approximately 45 degrees from a line 203 running longitudinally through apices 22a and the desired $M_r/M_p$ ratio is greater than 0.5. Previously known devices have a $M_r/M_p$ ratio less than 0.2 and ratios less than 0.2 tend to have more folding into the lumen.

Figure 3E:
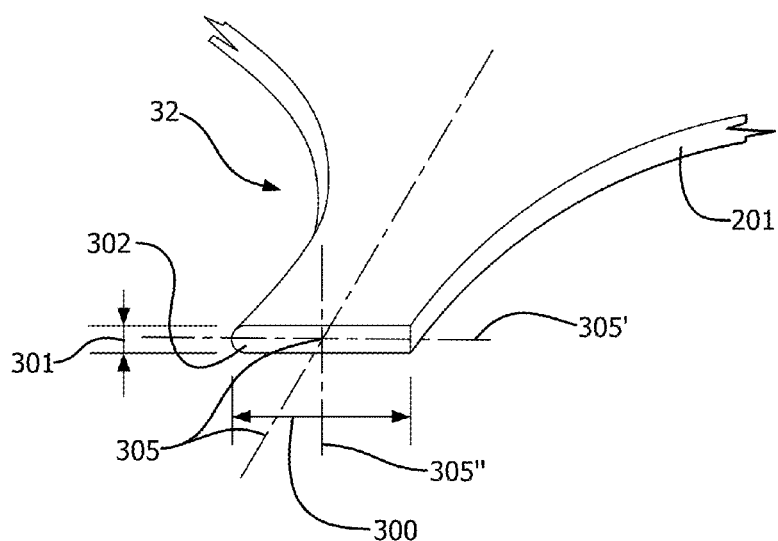
FIG. 3E is a representation of a perspective transverse cross section of a flexible connecting linkage with a $M_r/M_p$ ratio<0.2.

Perspective transverse cross sectional views of the flexible interconnecting elements 32 are shown in FIG. 3D and FIG. 3E. Web 32 may have a square or rectangular cross section 302. A square or rectangular cross section 302 can have neutral axes 305, 305' and 305". The neutral axes 305, 305' and 305" can be calculated by known means. Neutral axis 305 can be considered a longitudinal component of the neutral axes. A web width 300 of the web 32 that may be used in a section modulus calculation is measured along neutral axis 305' where 305' is a perpendicular component of the neutral axes. A web thickness 301 of the web 32 that may be used in a section modulus calculation is measured along neutral axis 305" where 305" is a radial component of the neutral axes. FIG. 3D is a representation of a cross section 302 that has a $M_r/M_p$ ratio greater than 0.2.

FIG. 3E shows a perspective view of a transverse cross section of polymeric web 32 from FIG. 2B of previously known art. The width 300 of the web 32 is typically much wider than the thickness 301 and the section modulus ratio $M_r/M_p$ is less than 0.2. When the section modulus ratio $M_r/M_p$ is less than 0.2, the linkages may have a greater tendency to fold more towards the luminal or abluminal space and out of the space defined by the inner circumference and outer circumference of the stent. In previously known devices the linkage width can be greater than 20 times the thickness and often is more on the magnitude of 50 times the thickness. The alternative webs described herein typically have widths less than 20 times the thickness. In an alternative embodiment, the width may be less than 10 times the thickness. In another alternative embodiment, the width may be less than 4 times the thickness. In still other alternative embodiments, the width may be less than the thickness. The width to thickness ratios required for "in plane" folding, may change depending on the angle 205 of the web 32 with respect to the centerline of the stent, or the length 208 of the web 32.

Figure 3F:
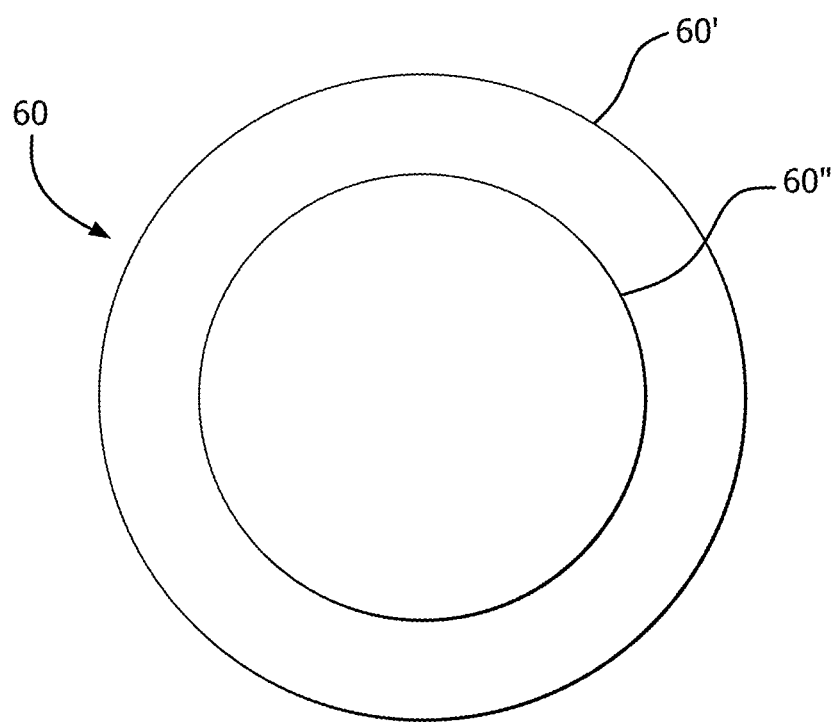
FIG. 3F is a transverse cross sectional representation of a stent showing the outer circumference and inner circumference of the stent.

FIG. 3F shows a transverse cross sectional view of an entire finished stent 60. "In plane" is defined as being substantially within the space between an outer circumference 60' or boundary and inner circumference 60" or boundary of the stent 60. "Out of plane" is defined as being substantially outside the space between the outer circumference 60' and inner circumference 60". Folding of a linkage may occur when the stent is compacted, e.g. circumferentially, diametrically, axially, bending, or longitudinally. One way of determining if the linkage folds "in plane" or "out of plane", is longitudinally compact the stent by approximately 20%, and evaluate if the linkage is substantially "in plane" or "out of plane" by the above definition.

Figure 3G:
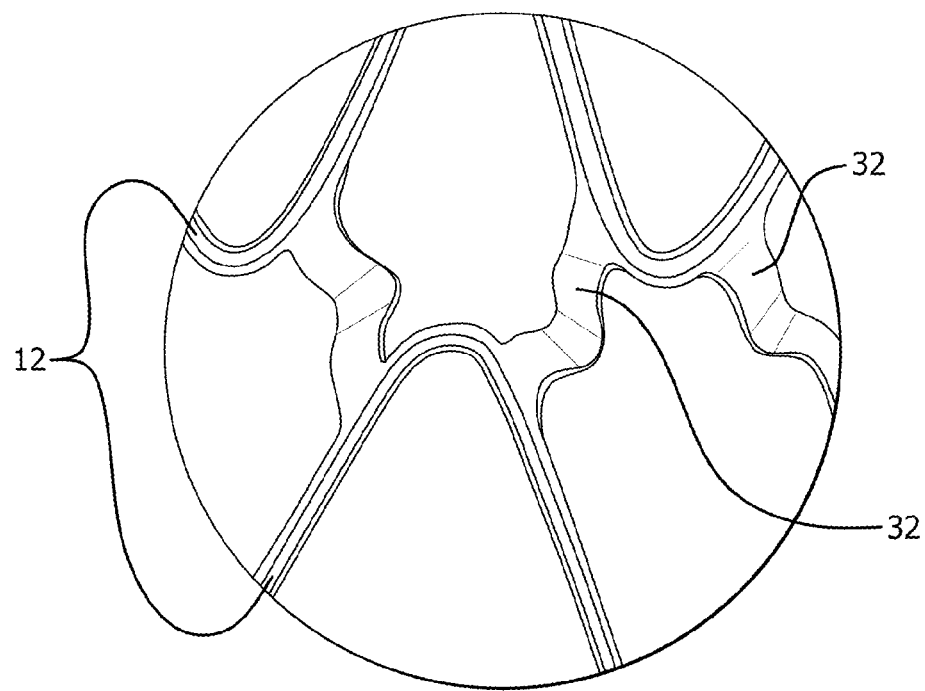
FIG. 3G is a perspective view of adjacent stent elements and a flexible connecting linkage folded substantially "out of plane".
Figure 3H:
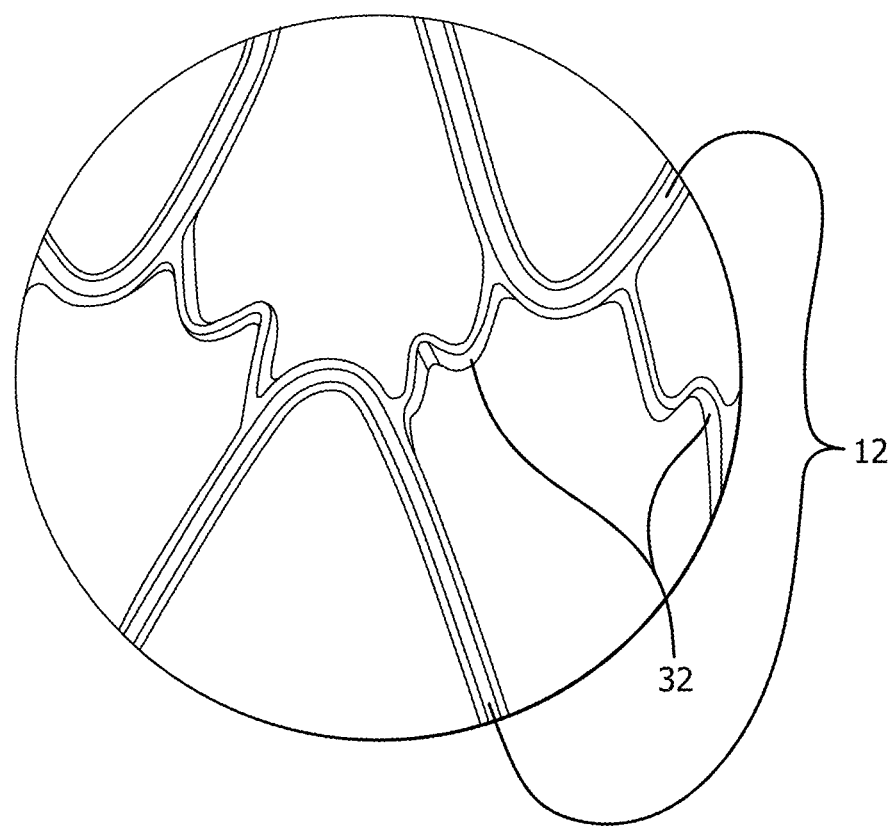
FIG. 3H is a perspective view of adjacent stent elements and a flexible connecting linkage folded substantially "in plane".

FIG. 3H shows a perspective view of a web 32 shown in FIG. 3D attached to adjacent stent elements 12 with a $M_r/M_p$ ratio greater than 0.2. The stent has been compacted and the web 32 is shown to fold substantially "in plane".

FIG. 3G shows a perspective view of a previously known web 32 shown in FIG. 3E attached to adjacent stent elements 12 with a $M_r/M_p$ ratio less than 0.2. The stent has been compacted and the web 32 is shown to fold substantially "out of plane".

Figure 3I:
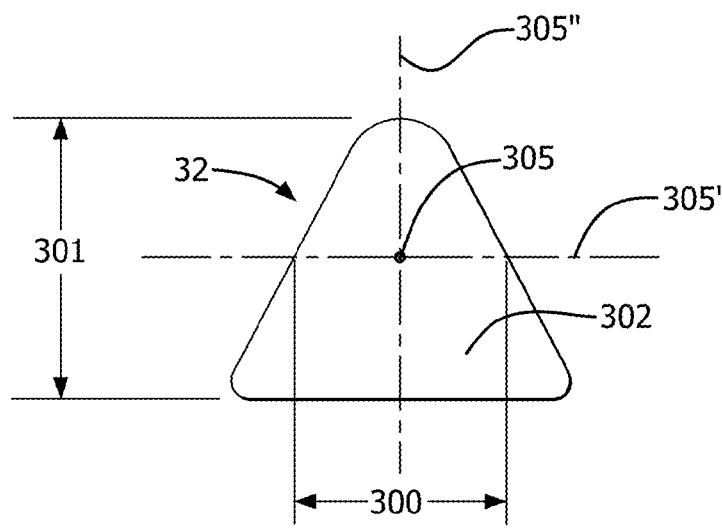
FIG. 3I and FIG. 3J show some alternative transverse cross sections of a flexible connecting linkage, both consistent with linkages shown in FIG. 2C and FIG. 2D, and representing a $M_r/M_p$ ratio>0.2.
Figure 3J:
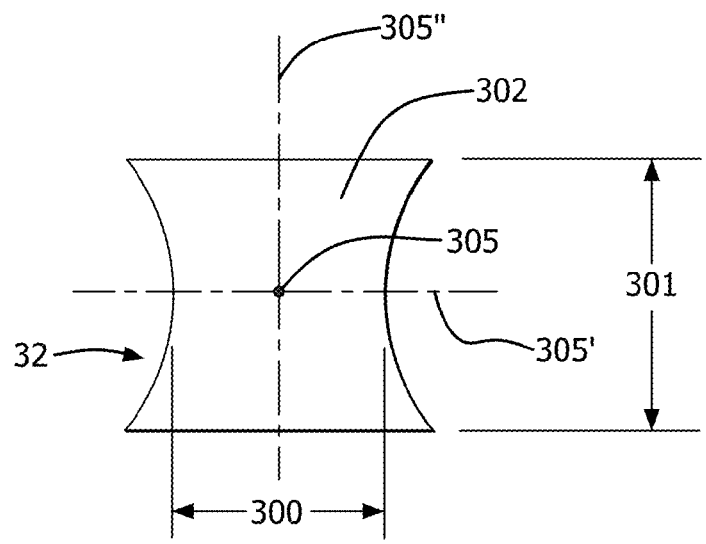

In various embodiments, polymer webs 32 have transverse cross sections 302, that may have different shapes, including but not limited to non-rectangular. For example, as shown in FIG. 3I the cross section 302 can have a triangular shape. The web 32 with the triangular cross section can be used for various purposes. For example, it could direct flow from a side branch vessel into a main branch vessel or from a main branch into a side branch. The transverse cross section 302 has neutral axes (305,305', and 305") and can be calculated by known means. The neutral axis 305 is a longitudinal component of the neutral axes (305,305', 305"). A web width 300 of the web 32 to use in a section modulus calculation is measured along neutral axis 305' where 305' is a perpendicular component of the neutral axes. A web thickness 301 of the web 32 to use in a section modulus calculation is measured along neutral axis 305" where 305" is a radial component of the neutral axes. In an alternative embodiment, the cross section can be hour glassed shaped as shown in FIG. 3J. In other embodiments, the cross section 302 can be of other shapes not explicitly shown.

Figure 3K:
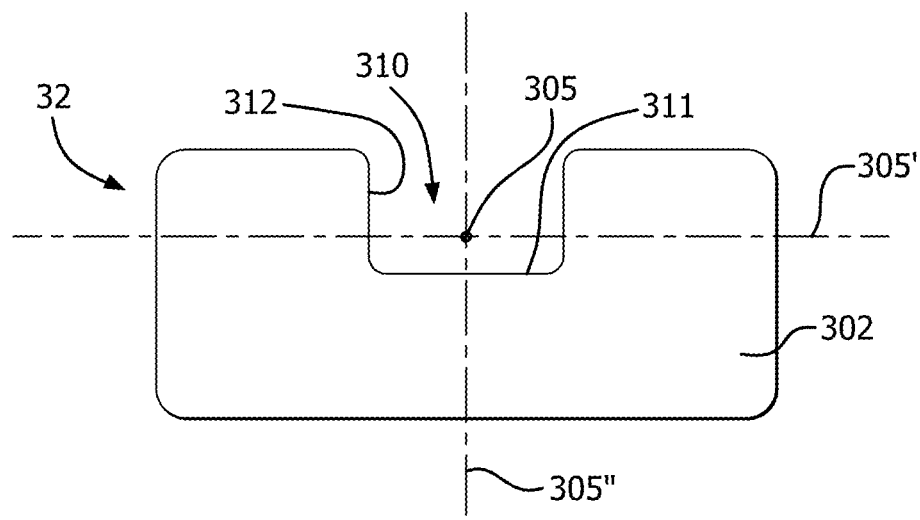
FIG. 3K shows a transverse cross sectional view of a flexible linkage with a reservoir embedded in the flexible connecting linkage.

FIG. 3K shows a cross section 302 that has a reservoir 310 in a polymer web 32. Polymer web 32 can be made to have a ratio $M_r/M_p>0.5$ even with the reservoir 310 in the polymer web as shown. The reservoir 310 can be made by laser cutting as described herein or other known methods. The laser cutting process can be tailored to create an area of adhesion 311 in the bottom of the reservoir 310. The reservoir side 312 is the side formed after laser cutting a reservoir 310 that is partially through the thickness of the polymer.

Figure 4:
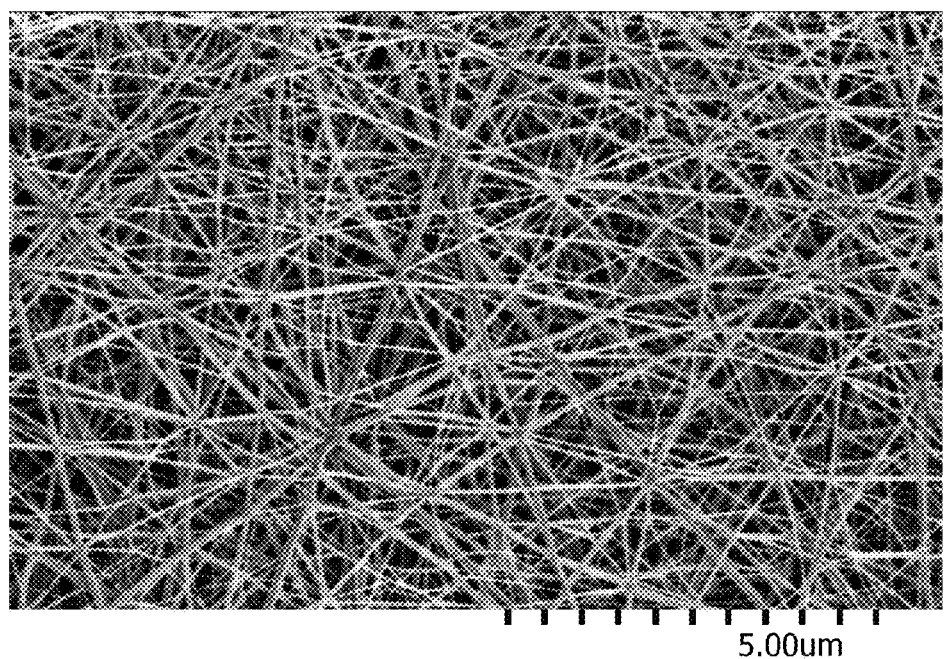
FIG. 4 is a scanning photomicrograph of a multiaxial ePTFE film useful for making the described open frame stent.

While various polymeric films may be suitable for use as the stent covering (or coating) material for this device, combinations of FEP (fluorinated ethylene propylene) films used in combination with ePTFE films are described herein. The ePTFE films described herein for use with these helically wound serpentine wire stents are films having multi-axial fibrillar orientations as shown by the scanning electron photomicrograph of FIG. 4. It is seen how the fibrils are oriented in all directions within the plane of the ePTFE film. ePTFE films of this type may be made as taught by U.S. Pat. No. 7,306,729 and US Published Patent Application 2007/

0012624 to Bacino et al. Films of this same type may optionally be provided with a partial covering of a thin layer of FEP (having openings through the FEP film covering; i.e., a discontinuous covering). FEP coated ePTFE films, with either a discontinuous (porous) FEP covering (coating) or a continuous (non-porous) FEP covering (coating) may be made generally as taught by U.S. Pat. No. 5,735,892 to Myers et al.

While, as noted, various types of films may be used for the stent covering, the described ePTFE films has a multiaxial (within the plane of the film) strength orientation. It is strong, thin, and has excellent biocompatibility. When suitable heat is applied following slitting, the film will retract (shrink back) with good uniformity to create the openings 34 through the polymeric stent covering and to create the flexible polymeric interconnecting webs 32 between adjacent stent elements. Different films or films with different heat retraction characteristics can be stacked on top of each other or layered such that the film retracts to form cross sections such as those shown in FIG. 3I and FIG. 3J.

Figure 5A:
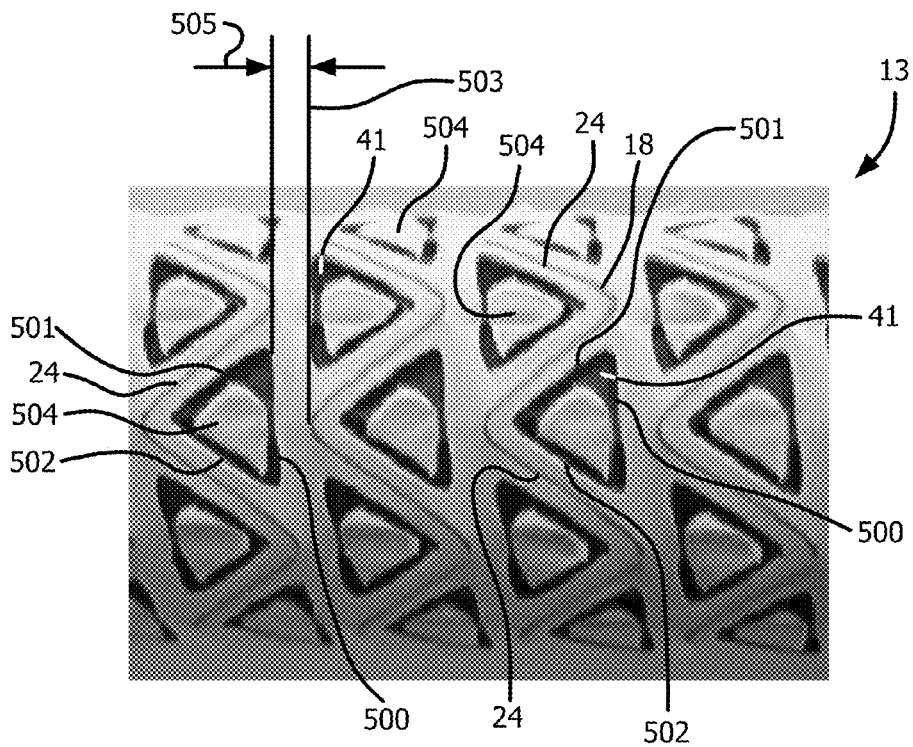
FIG. 5A shows a perspective view of a partially completed stent provided with multiple slits or openings to create enclosed apertures with islands of material remaining within the apertures that are part of the process of manufacturing device embodiments described herein.
Figure 5B:
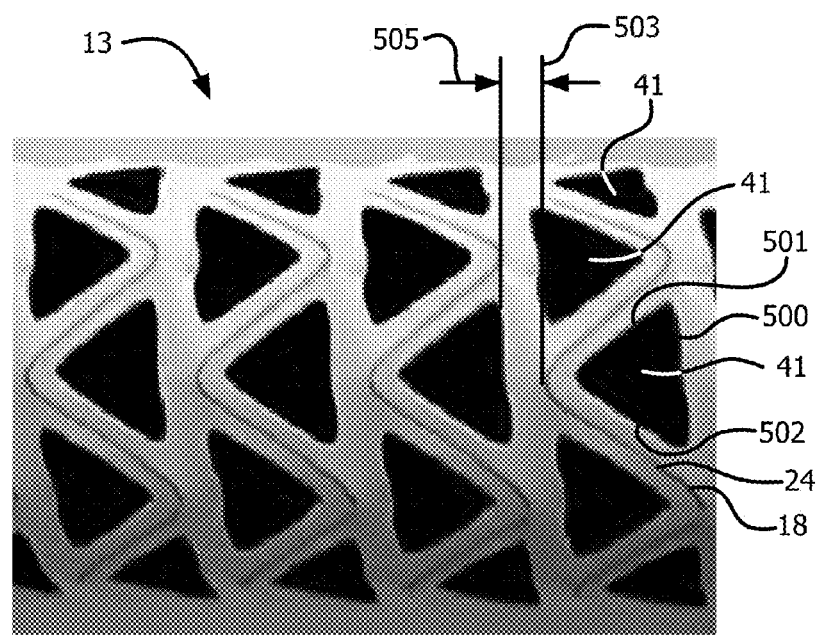
FIG. 5B shows a perspective view of the partially completed stent shown in FIG. 5A with the islands of material removed that are part of the process of manufacturing device embodiments described herein.

FIGS. 5A and 5B show a partially finished stent 13 of helically wound serpentine wire 18 provided with a first outer (abluminal) covering of FEP film and an additional covering of multiaxial ePTFE film, wherein apertures 41 (e.g., multiple continuous slits to form a triangle enclosure) have been made through the film between adjacent apices of the wire that are pointed in the same direction. In some embodiments, after the film has been slit, forming the apertures or triangular enclosures as shown, islands 504 of the ePTFE film can be left behind as shown in FIG. 5A. These islands 504 can be removed, (e.g. by using a vacuum device) and thus forming larger openings 41 as shown in FIG. 5B prior to heating the film. Heat can then be applied to the device having apertures 41, causing the film(s) to shrink back toward the adjacent wire stent elements, subsequently resulting in the openings 34 in a finished stent 60 as shown in FIG. 2C.

A method of making a flexible stent is as follows. A stainless steel mandrel of diameter equal to about the inside diameter of the intended stent is obtained. The mandrel surface is provided with exterior grooves to accommodate and locate the structural elements of the stent. In one embodiment such as shown, for example, in FIG. 2D the stent has amplitude 27 of 0.108 inches (2.743 mm) and a wavelength 29 of 0.124 inches (3.150 mm). The amplitude 27 is the distance from a distal apex 22a of one stent element 12 to the distal apex 22a of an adjacent stent element 12 where the two distal pointing apices 22a are pointing in the same direction. The straight segment 24 of the stent 10 in one embodiment is 0.153 inches (3.886 mm) approximately. A shallow groove mandrel has grooves wrapped in the same pattern as the stent was wound, but at a depth of 0.002 inches (0.0508 mm) compared to a larger depth, e.g. 0.0024 inches (0.061 mm) that is used for the stent winding process. The depth of the shallow groove mandrel depends on the wire diameter of the stent but for a 0.012 inch (0.305 mm) to 0.018 inches (0.457 mm) wire, a depth of 0.002 inches (0.0508 mm) deep is acceptable. In this case, a 12 mm diameter mandrel was used with a 0.012 inch (0.305 mm) diameter wire and a 0.002 inch (0.0508 mm) deep shallow groove mandrel is used. A stent of the desired length and diameter made of helically wound serpentine nitinol wire is provided (wire diameter as desired). This is then wound around the surface of the shallow groove mandrel such that the stent is sitting in the grooves and the apices of the serpentine wire are aligned so that apices pointing in a common direction are aligned with and parallel to the longitudinal axis of the mandrel. The end of the stent wires are secured to an adjacent winding of the stent wire using an FEP thread tied with a securing knot. The stent is then helically wrapped with a covering of a single layer of FEP tape that has been cut from FEP film (0.00015 inch thickness or 0.0038 mm and about 0.75 inch width or 19.05 mm), and stretched tightly over the outer surface of the stent with minimal overlap of adjacent edges of the FEP tape. This FEP tape is then cigarette wrapped (wrapped in a direction perpendicular to the longitudinal axis of the mandrel) with an ePTFE film of the type described previously. This wrapping may be started by aligning a transverse edge of the film with the longitudinal axis of the mandrel and attaching it to the underlying FEP film by carefully melt-bonding the ePTFE film edge to the FEP using a heat source such as a clean soldering iron or appropriate equivalent. Twelve layers of the ePTFE film are wrapped around the outer surface of the stent and the film edge is trimmed along the length of the stent (i.e., parallel to the longitudinal axis of the mandrel). The film edge is secured with the previously used heat source.

As shown in FIGS. 5A and 5B, shaped apertures, or openings 41, are created between adjacent wire apices that are pointed in the same direction. These apertures 41 may be created by any suitable means, including the use of a scalpel blade, water jet, laser, etc. One such suitable laser is a Coherent Inc., Model: GEM-100A, CO.sub.2, CW (continuous wave only), Santa Clara, Calif. The size of these shaped apertures 41 is dependent on the desired width 300 of the flexible connecting element 32. The laser cut aperture 41 was cut in a triangle shape such that legs 501 and 502 (after retraction at least a portion of the legs 501 and 502 become the vestigial edges 36) of the triangle were offset from the straight portions or segments 24 of the wound stent by 0.030 inches (0.762 mm) and the circumferentially oriented remaining leg 500 (after retraction at least a portion of leg 500 can become shaped section 202) was offset a distance 505 of approximately 0.031 inches (0.787 mm) from the adjacent apical tangent line 503. After the heat retraction step the width of the linkage was approximately 0.007 inches (0.178 mm) wide and approximately 0.003 inches (0.076 mm) thick. This allowed for the linkage to fold substantially in plane with a $M_r/M_p$ ratio>0.4. The width and thickness of the polymer web 32 can be further tailored to make the web 32 closer to a $M_r/M_p$ ratio>0.5. The thickness 301 of the linkage 32 may be in the range of 0.002 inches (0.0508 mm) to 0.004 inches (0.102 mm) but may in alternative embodiments be in the range of 0.0005 inches (0.0127 mm) to 0.007 inches (0.178 mm). The width of the linkage 300 may be about 0.007 inches (0.178 mm), but can alternatively be in the range of 0.003 inches (0.076 mm) to 0.022 inches (0.559 mm). The last row of apices at each end of the stent may be omitted from apertures if it is desired to leave these end rows covered in their entirety (i.e., in stent-graft fashion). The entire length of the wrapped stent is then provided with a temporary helical wrap of Kapton®Polyimide Film tape (Dupont, 0.002 inch or 0.0508 mm thickness); the ends of this tape may be secured to the surface of the mandrel beyond each end of the stent with a mechanical clip or other temporary fastener. This layer of Kapton is then tightly wrapped with a temporary helical wrap of ePTFE tape (made from an ePTFE film having a fibrillar microstructure with fibrils oriented predominately parallel to the length of the tape and wrapped with a small pitch angle so that the orientation is primarily circumferential with respect to the mandrel). This ePTFE tape will provide circumferential compression to the underlying materials when suitably heated.

The above construction can then be placed into a suitable convection oven set at 370 degree C. for 17 minutes, after which it can be removed from the oven and allowed to cool to approximately ambient temperature. As one of ordinary skill in the art can appreciate, the times and temperatures can be varied slightly to achieve desired results. The outer layers of ePTFE film and Kapton tape are then removed. The resulting coated stent and underlying layer of Kapton tape are then carefully removed from the mandrel. Remaining film edges protruding beyond the ends of the stent may then be carefully trimmed in a transverse direction close to the end apices of the stent wire with a scalpel blade.

Figure 6:
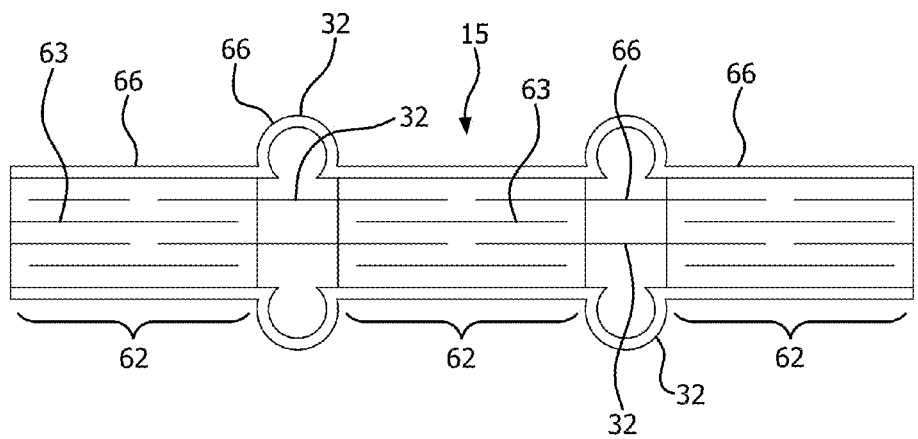
FIG. 6 is a side view of previously known art wherein flexible connecting elements fold substantially outside the space located between the outer surface of the metallic stent and the inner surface of the metallic stent, i.e. "out of plane".

FIG. 6 is a schematic side view of a previously known stent 15 as it would appear mounted on a balloon (not shown) for subsequent deployment and expansion where the webs 32 are bowed or wrinkled, and "out of plane", when previously known stent 15 is foreshortened.

Figure 7A:
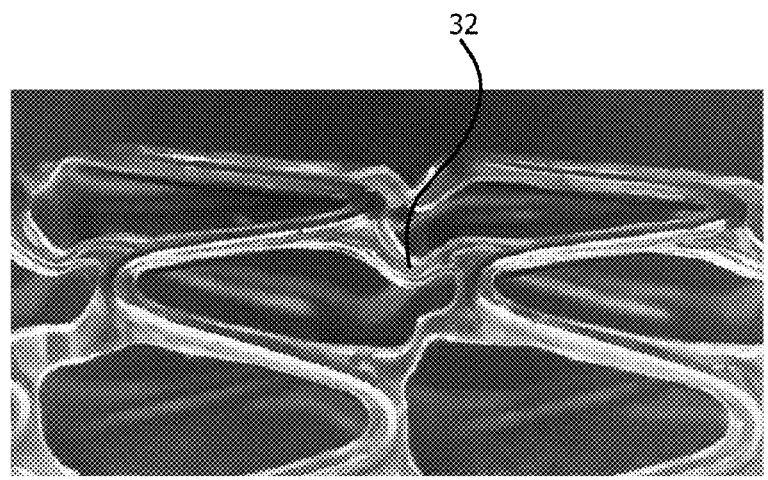
FIG. 7A is a perspective magnified photographic image of previously known art in partial longitudinal compression showing how the flexible connecting linkages fold "out of plane".

FIG. 7A shows a magnified photographic image (approximately 13×) of previously known device in a partially longitudinally compressed state with a $M_r/M_p$ ratio<0.2 and the webs fold substantially luminally inward and consequently folding out of plane (i.e., are folded inward to the extent that they extend inward beyond the space defined between the outer and inner circumferences of the stent). The webs tend to stay in this configuration as long as a compaction force is applied. In this case, the compaction force was a longitudinally applied force that shortened the overall length of the stent.

Figure 7B:
FIG. 7B is a perspective magnified photographic image of previously known art at or near full longitudinal compression showing how the flexible connecting linkages fold "out of plane".
Figure 7C:
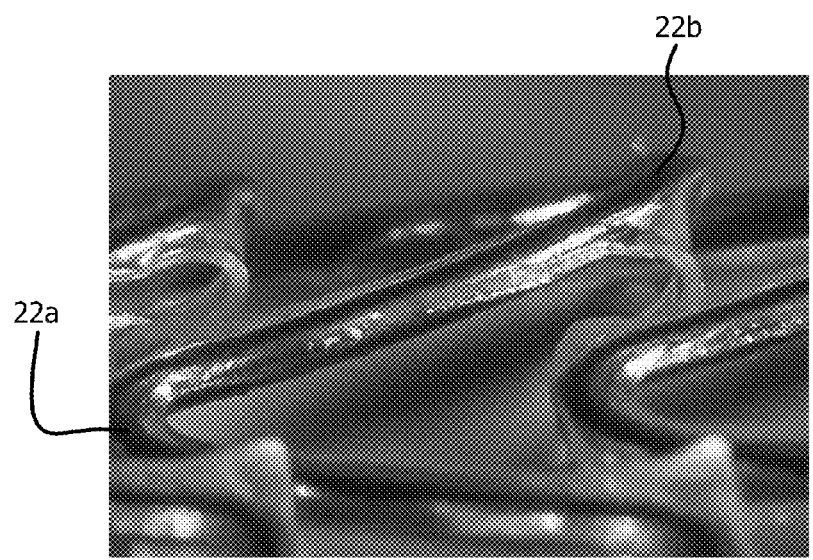
FIG. 7C is a perspective magnified photographic image of previously known art at or near full longitudinal compression showing how apices on one side of an individual winding are raised further away from the longitudinal axis of the stent, by the prior art connecting linkage, in comparison to apices on the opposite side of the same individual winding.

FIG. 7B shows a magnified photographic image of a previously known stent in substantially a fully longitudinally compressed state with the linkages folding out of plane. FIG. 7C is another view of the stent shown in FIG. 7B showing how the apices of an individual winding are at different distances from the longitudinal axis of the stent, which appears to be a result of the linkages folding out of plane during longitudinal compression of the stent.

Figure 8A:
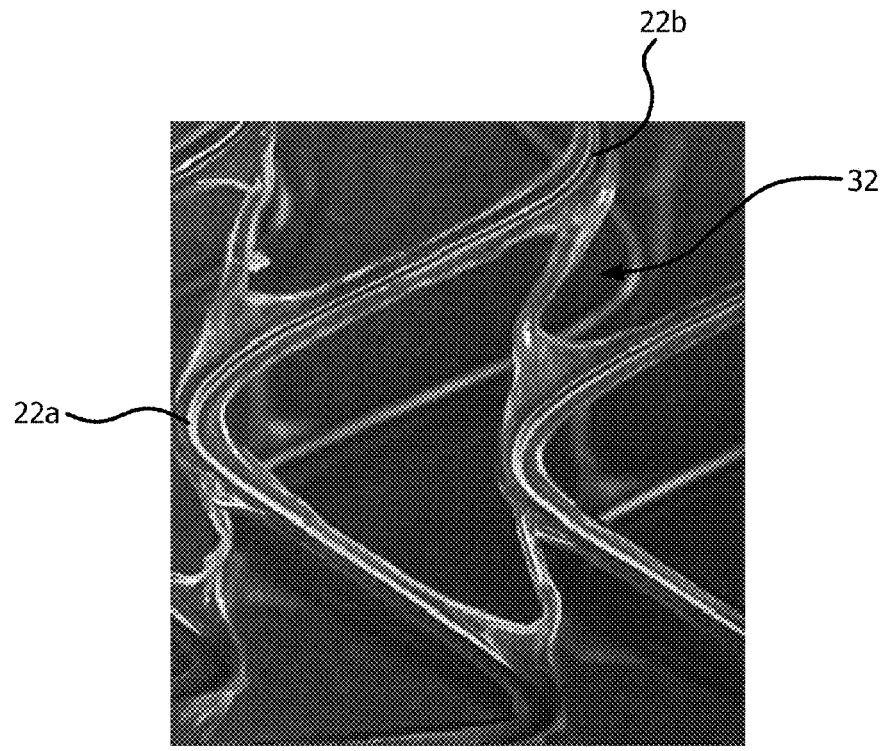
FIG. 8A is a perspective magnified photographic image of a stent in accordance with an embodiment wherein the flexible connecting linkages fold substantially "in plane" when the stent is in a longitudinally compressive state and the linkages are significantly limiting the longitudinal compression.
Figure 8B:
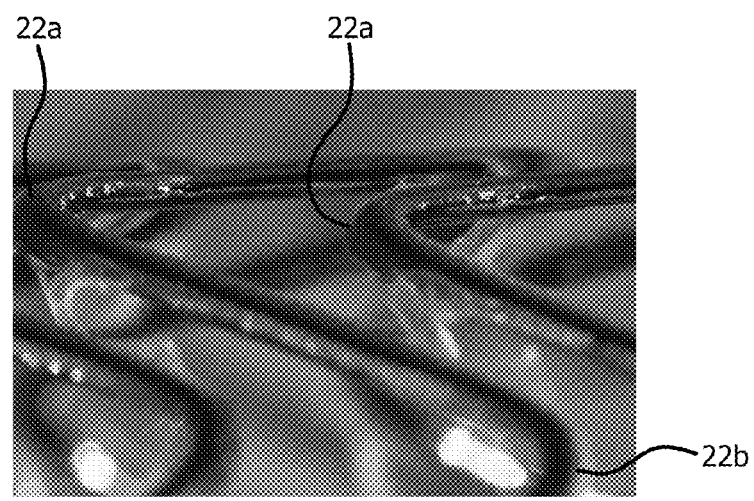
FIG. 8B is a perspective magnified photographic image of a stent with linkages that fold "in plane" and where the apices on one side of an individual winding are at substantially the same distance from the longitudinal axis of the stent as the apices on the opposite side of the same individual winding (as opposed apex height relationship shown in FIG. 7C of the prior art).

FIG. 8A shows a magnified side photographic image (approximately 8×) of a stent with a $M_r/M_p$ ratio>0.2 in a partially longitudinally compressed state where the webs 32 fold substantially "in plane". FIG. 8B is a magnified photographic image of a substantially fully longitudinally compressed stent with linkages or webs folding substantially in plane. The opposing apices 22a and 22b of any one individual winding are substantially at the same distance from the longitudinal axis of the stent. This phenomenon can be largely attributed to the linkages folding in plane.

Figure 9A:
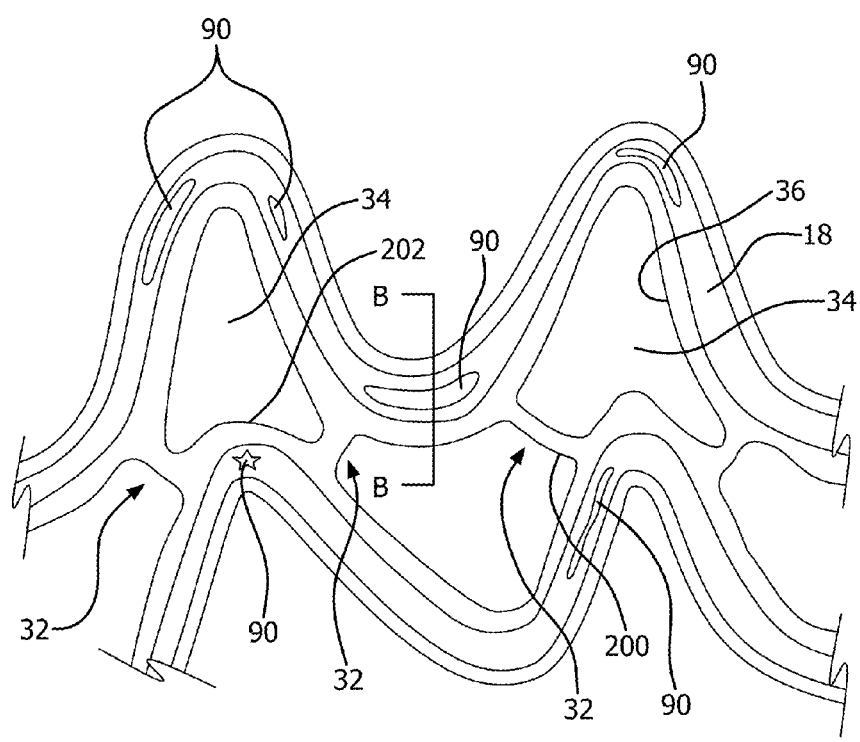
FIG. 9A is a plan view of a stent in accordance with an embodiment, wherein the flexible connecting linkage that covers the metallic structure has a discontinuous portion only above a portion of the metallic structure.

In various embodiments a reservoir 90 can be formed in a covering (e.g. ePTFE) along a metallic structure (e.g. wire 18). For example, as shown in FIG. 9A, a reservoir 90 can be formed into the ePTFE covering along the serpentine wire 18 of a stent. The reservoir 90 can be through the full thickness of the ePTFE covering or partially through the thickness. If the reservoir 90 is through the full thickness versus partially through the thickness, the stent frame is exposed. The reservoirs can take on various shapes.

Figure 9B:
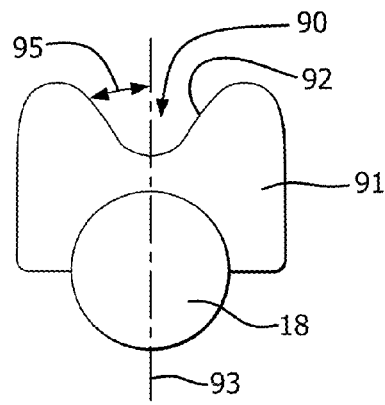
FIGS. 9B-9G show transverse cross sections of the reservoir and the metallic structure.
Figure 9C:
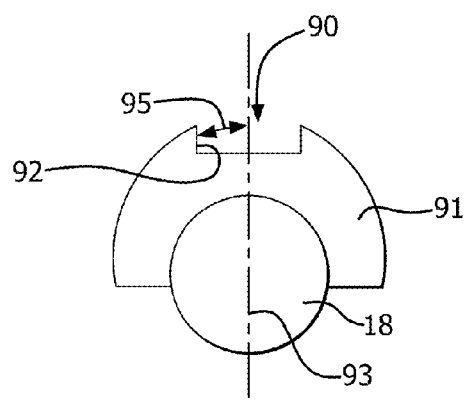
Figure 9D:
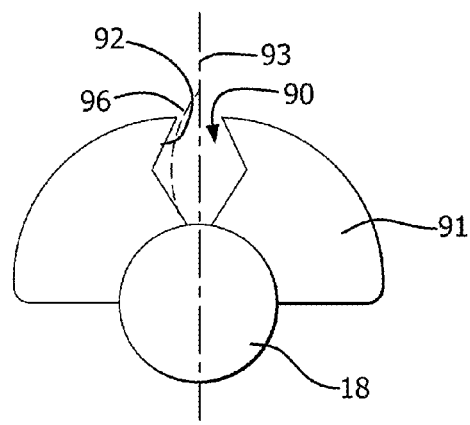
Figure 9E:
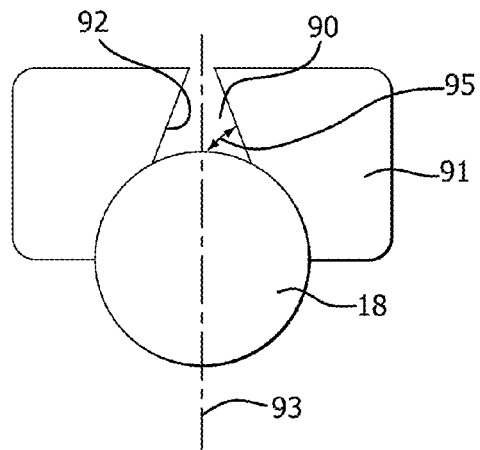
Figure 9F:
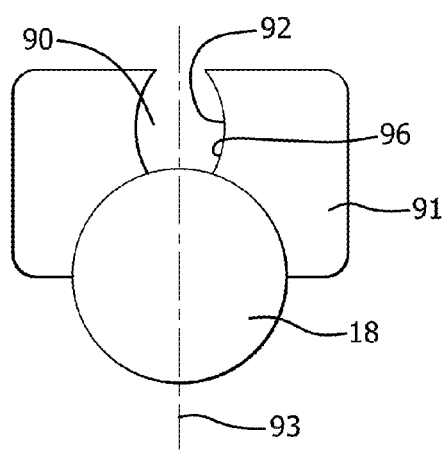
Figure 9G:
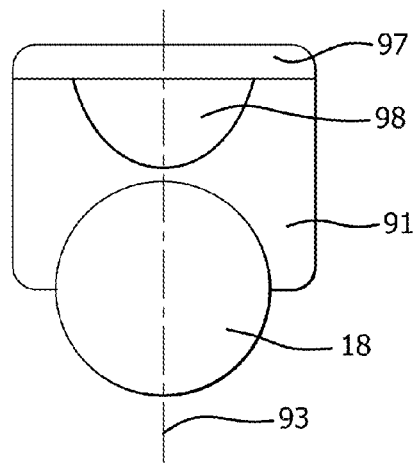

In various embodiments, a stent may have a reservoir 90 along a wire 18 and the stent may have a wire and polymer reservoir cross section 91. For example, as shown in the transverse cross sections B-B of FIGS. 9B-9G from FIG. 9A, the wire and polymer reservoir cross section 91 has a reservoir side wall 92. The reservoir sidewall 92 can have various angles 95 with respect to a center line or plane 93. For example, as shown in FIG. 9B, the sidewall 92 has an angle between 0 degrees and 90 degrees. The sidewall 92 may alternatively have an angle of zero degrees as shown in FIG. 9C. The sidewall 92 may also have an angle greater than 90 degrees. The sidewall 92 may have multiple angles, for example some are greater than 0 degrees and some are less than 0 degrees with respect to the vertical perpendicular plane 93, and substantially create an arcuate shape 96 as shown in FIG. 9D. The side walls 92 may have angles 95 less than zero degrees as shown in FIG. 9E. Furthermore, the sidewalls 92 may be configured as a continuous sidewall to create an arcuate shape 96 with respect to a center line 93 where the sidewall 92 is concave as shown in FIG. 9F. The sidewalls 92 could also be convex. Other shapes and combinations of these shapes mentioned can also be made. In various embodiments, a reservoir 90 can be covered. For example, as shown in FIG. 9G, an additional layer or covering 97 can be applied along the stent 10 to create an enclosed reservoir 98. The covering may also be permeable or impermeable. If permeable it can slowly release an agent.

Figure 10A:
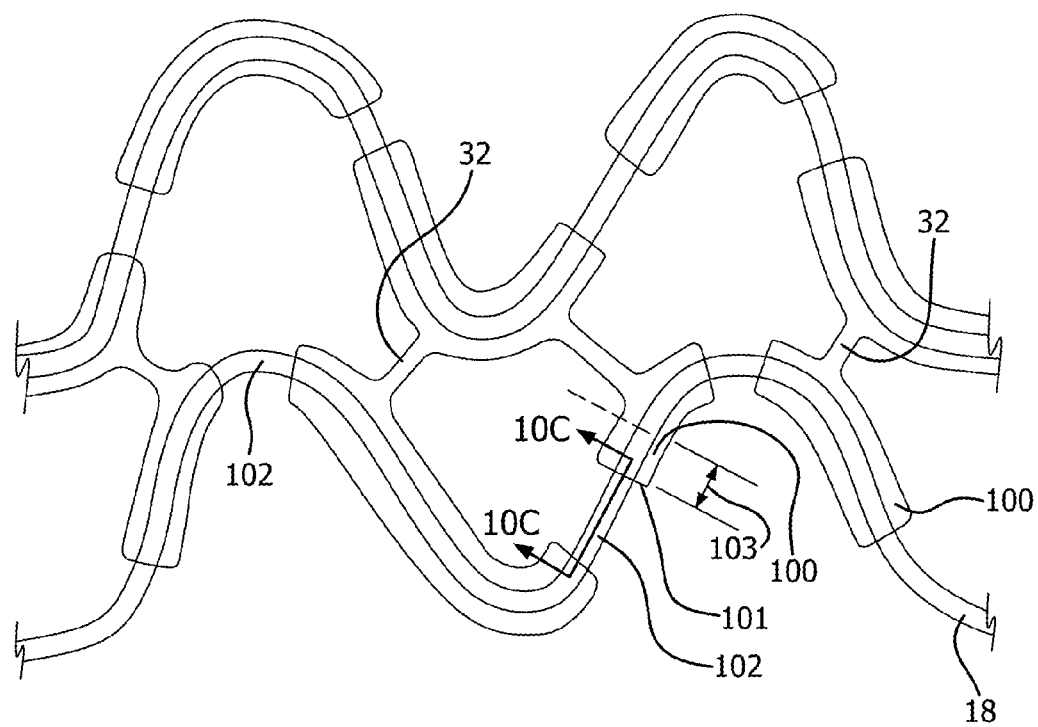
FIGS. 10A and 10C are plan views of a stent in accordance with an embodiment, wherein the polymer webs have extensions covering a portion of the metallic stent structure.
Figure 10B:
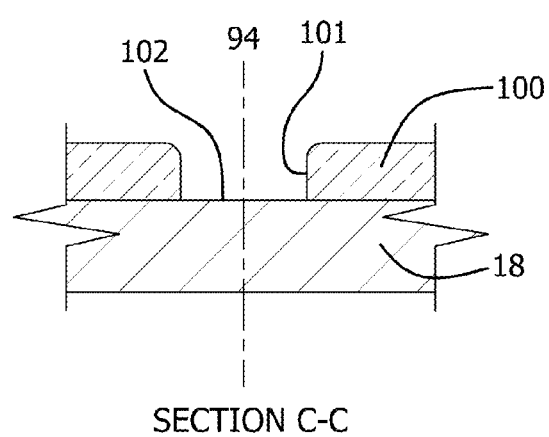
FIGS. 10B and 10D show a transverse cross section of the web extensions along a length of the metallic stent structure.
Figure 10C:
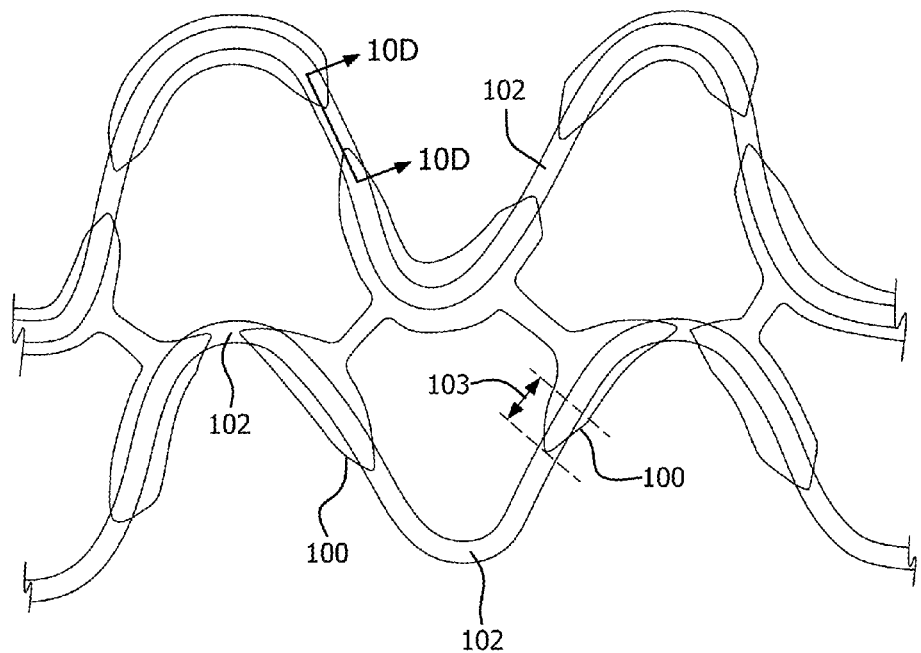
Figure 10D:
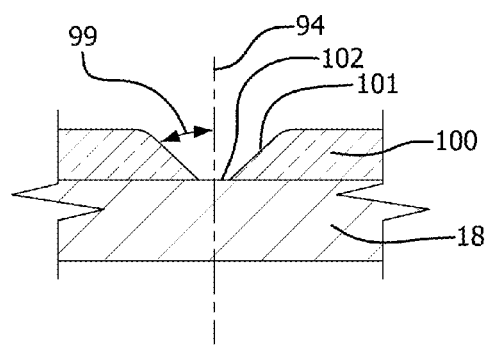

In various embodiments, a covering or a polymeric web 32 can have web extensions 100 and be discontinuous along a metallic structure such as a wire 18. For example, as shown in FIG. 10A the web 32 has an extension 100 that may extend beyond the shaped portion 201 along a wire 18. The extension 100 has a length 103 that may extend along the wire 18. In various embodiments the extension 100 has a sidewall 101. As shown in cross section C-C in FIG. 10B, the sidewall 101 may be perpendicular to a vertical plane or line 94. Furthermore, as shown by example in FIG. 10C, the web extension 100 can have a nose cone shape. As shown in cross section D-D in FIG. 10D, the sidewall 101 may have an angle 99 in relation to vertical plane 94. The extensions 100 can be created by laser removing the covering or by an etching process. These extensions 100 can provide sufficient attachment of the web 32 to the stent 10 while also providing an additional location on the stent frame for other material or therapeutic agents or for creating adhesion zones 102 (the area of the exposed stent frame that is between adjacent web foot extensions 100). The adhesion zones 102 can be the exposed stent frame or the exposed stent frame can be treated by known methods to allow for better vessel attachment or be treated for any desired clinical response. These adhesion zones 102, can act as "stop points" or a location for a constraining covering to rest or stop against (e.g. during a deployment).

Figure 11A:
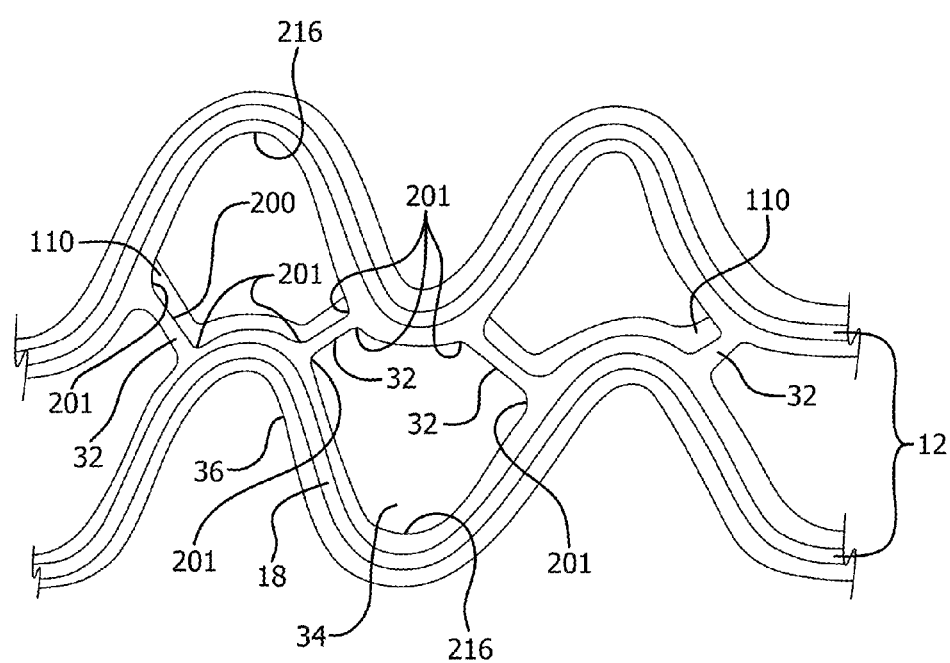
FIG. 11A is a plan view of a stent in accordance with an embodiment, wherein the polymer webs have a reinforcement section.
Figure 11B:
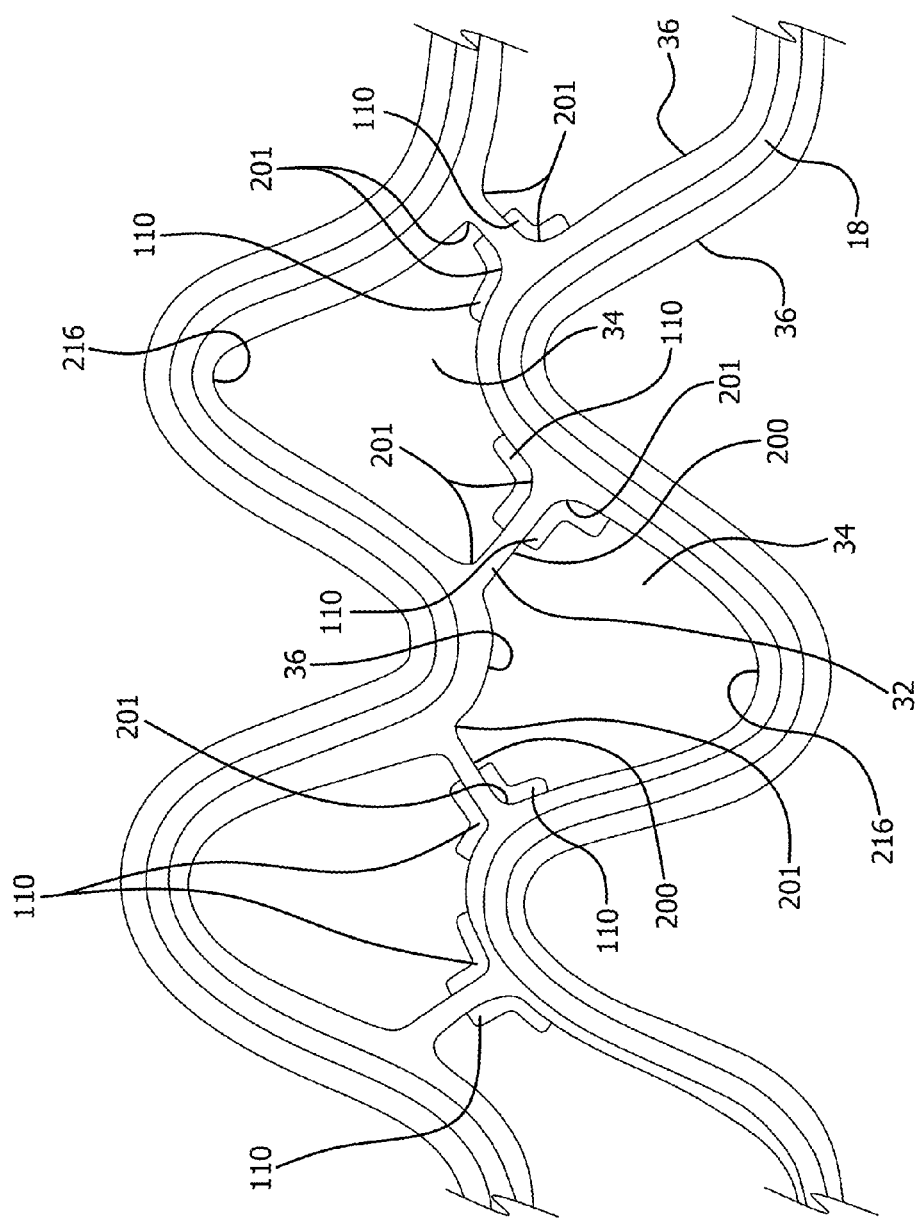
FIG. 11B is a plan view of a stent wherein polymer webs have an alternative configuration of a reinforcement section.

In various embodiments, a web or metallic structure may have an added reinforcement section. For example, as shown in FIGS. 11A and 11B, web 32 has added web reinforcement section 110. The web reinforcement section 110 can be an added on piece such as a metallic section that attaches or snaps onto the web 32 as shown, or it can be attached in any other means including using an adhesive. The web reinforcement section 110 can alternatively be a part of the polymeric web 32 wherein a portion of the web is densified or cured by any means including a laser. For example, the web may be densified along a straight portion 200 of the web 32. Web reinforcement section 110 can be attached before or after the heat retraction step mentioned above in this document. The web reinforcement section 110 can be of any dimension, to get desired web stiffness, but a metallic reinforcement section can be used in a range of 0.0005 inches (0.0127 mm) to 0.010 inches (0.254 mm) equivalent diameter.

The web reinforcement section 110 in FIG. 11A is shown on one side of the polymer webs 32. Alternatively, the reinforcement section 110 may also be on an opposite side such that the reinforcement section 110 is on two sides of the polymer web 32 and the reinforcement sections 110 are in two distinct apertures 34 as shown in FIG. 11B. The web reinforcement sections 110 can also be used to reinforce mainly the shaped portion (e.g. curved) 201 of the polymer web 32 as shown in FIG. 11B, but may also reinforce the straight portion 200. The reinforcement feature 110 may also be along a vestigial edge 36 along an apex 22a. The reinforcement feature 110 can be located just distal of apex 22a and follow the contour of an opening 34. It may follow the entire inside boundary of the opening 34 or it may only partially follow the boundary. The reinforcement feature 110 can be incorporated to the wire 18 through a via located in the vestigial edge 36. If a vestigial edge 36 does not exist, the reinforcement feature 110 can attach directly to the wire 18. A web reinforcement may alternatively be along a web length 208 and may be deposited on the web 32, e.g. a metallic coating that is sputtered or vapor deposited on or by other known means.

In the case where the reinforcement feature 110 is made out of a polymer that is similar to the polymer web, the reinforcement feature can have a different density or porosity such that there is a distinct line that is visible between the web 32 and the reinforcement feature. The distinct line or interface can be viewed under a Scanning Electronic Microscope (SEM). The reinforcement feature can be made by laser adjustments or other known methods. FIGS. 11A and 11B show various configurations and shapes of the reinforcement section 110 and are not intended to be limiting as to what the configurations can be.

The reinforcement section 110 can be advantageous if an increase in radial stiffness is desired but fatigue resistance is of concern. Previously known designs increase the diameter 25 of wire 18 or increase the metallic stent structure wall thickness to increase radial stiffness. A potential trade off to increasing the wall thickness or wire diameter is a decrease in fatigue resistance. This web modification is a potential way to increase radial stiffness without decreasing fatigue resistance and perhaps, depending on the design, without increasing profile.

Figure 11C:
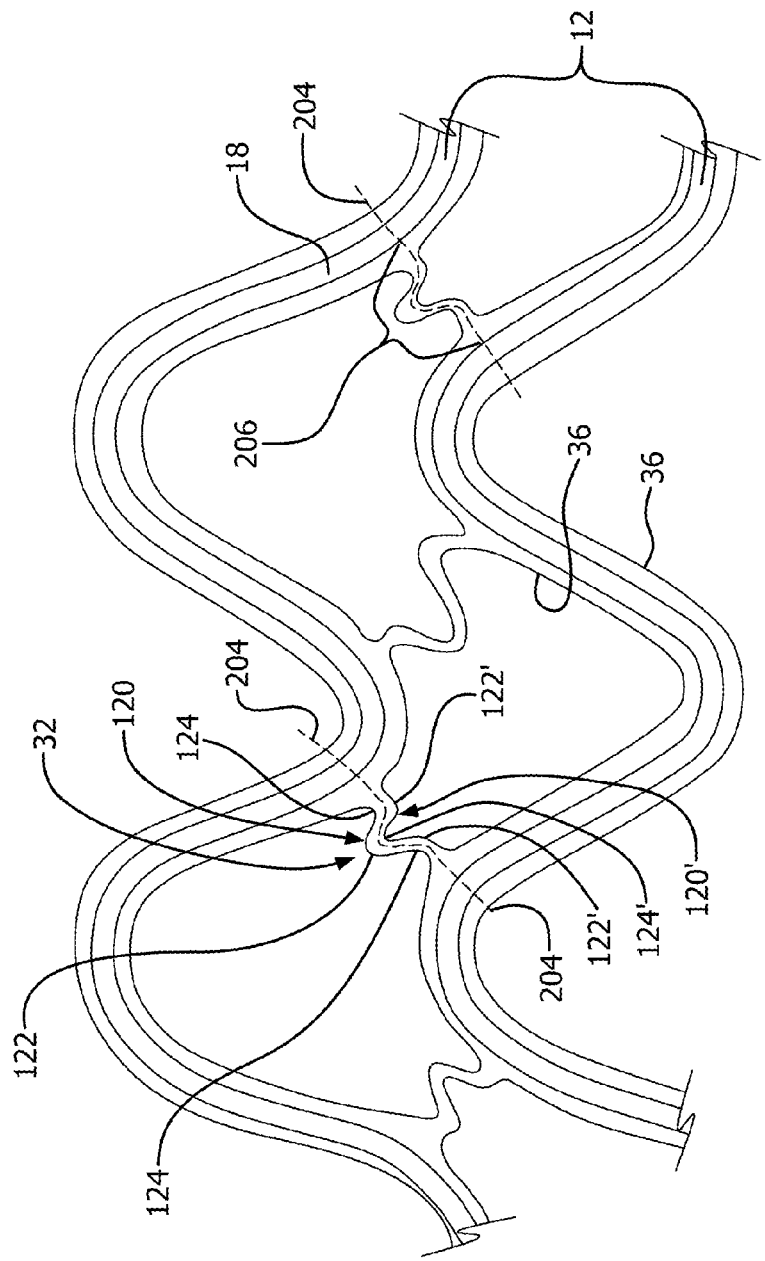
FIG. 11C is a plan view of a stent in accordance with an embodiment wherein the polymer webs have an undulation when the stent is in a relaxed configuration (e.g. minimal longitudinal tension or longitudinal compression being applied to the stent).

In various embodiments, a polymer web may have a tortuous path along a length when the stent is in a relaxed configuration. For example, as shown in FIG. 11C, the polymer web 32 can have a tortuous path along its tortuous length 206 where an individual edge 120 has at least two concave shapes 124 and one convex shape 122 (as viewed from within the opening the edge borders) and the opposite edge 120' has at least two convex shapes 122' (e.g. a mirror image along centerline 204, of the concave shape 124) and at least one concave shape 124' (e.g. a mirror image along centerline 204, of the convex shape 122). The tortuous path may be along the centerline 204. The centerline 204 may be drawn as a line of symmetry along web 32. The undulating shape of the polymer web 32 may aid in creating polymer web 32 that folds substantially with in the outer diameter of the stent and the inner diameter of the stent, i.e. "in plane". The edge 120 is along the polymer web 32 that spans the space between the adjacent stent elements 12. The edge 120 is distinct from the vestigial edge 36. The undulating polymer web 32 has a tortuous length 206 as measured along web centerline 204 that is longer than a straight, or non-undulating web, would have in the approximate same position. The length 206 is the distance along web 32 (e.g. the distance along the symmetric centerline 204 spanning between adjacent stent elements 12). A tortuous length 206 in some cases may be 10% longer or more than if the centerline 204 was straight and did not follow the tortuous path.

Figure 11D:
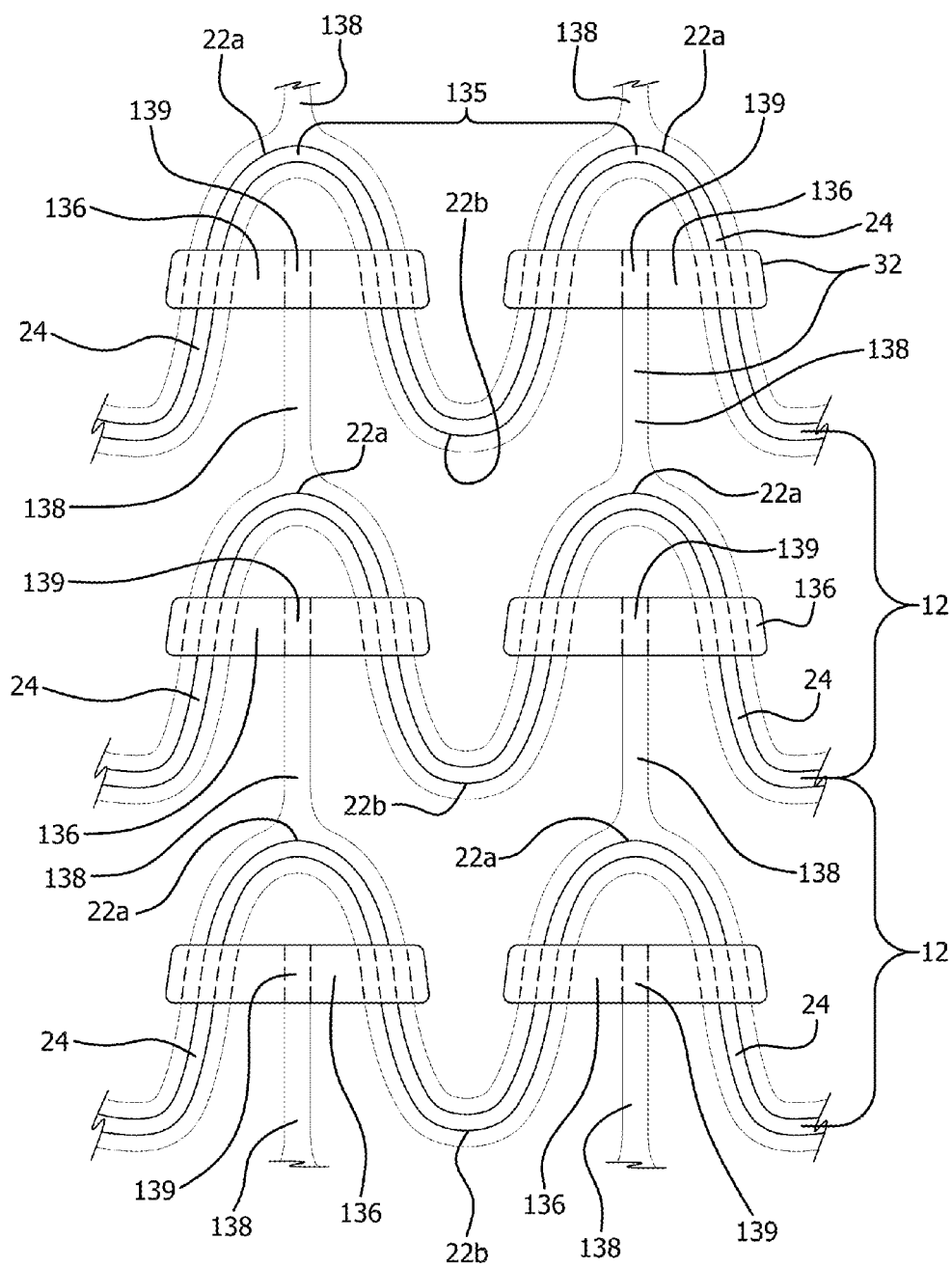
FIGS. 11D, 11E and 11F each show a plan view of a stent in accordance with one embodiment wherein the stent has flexible connecting elements made up of an elastic portion and a non-elastic portion.
Figure 11E:
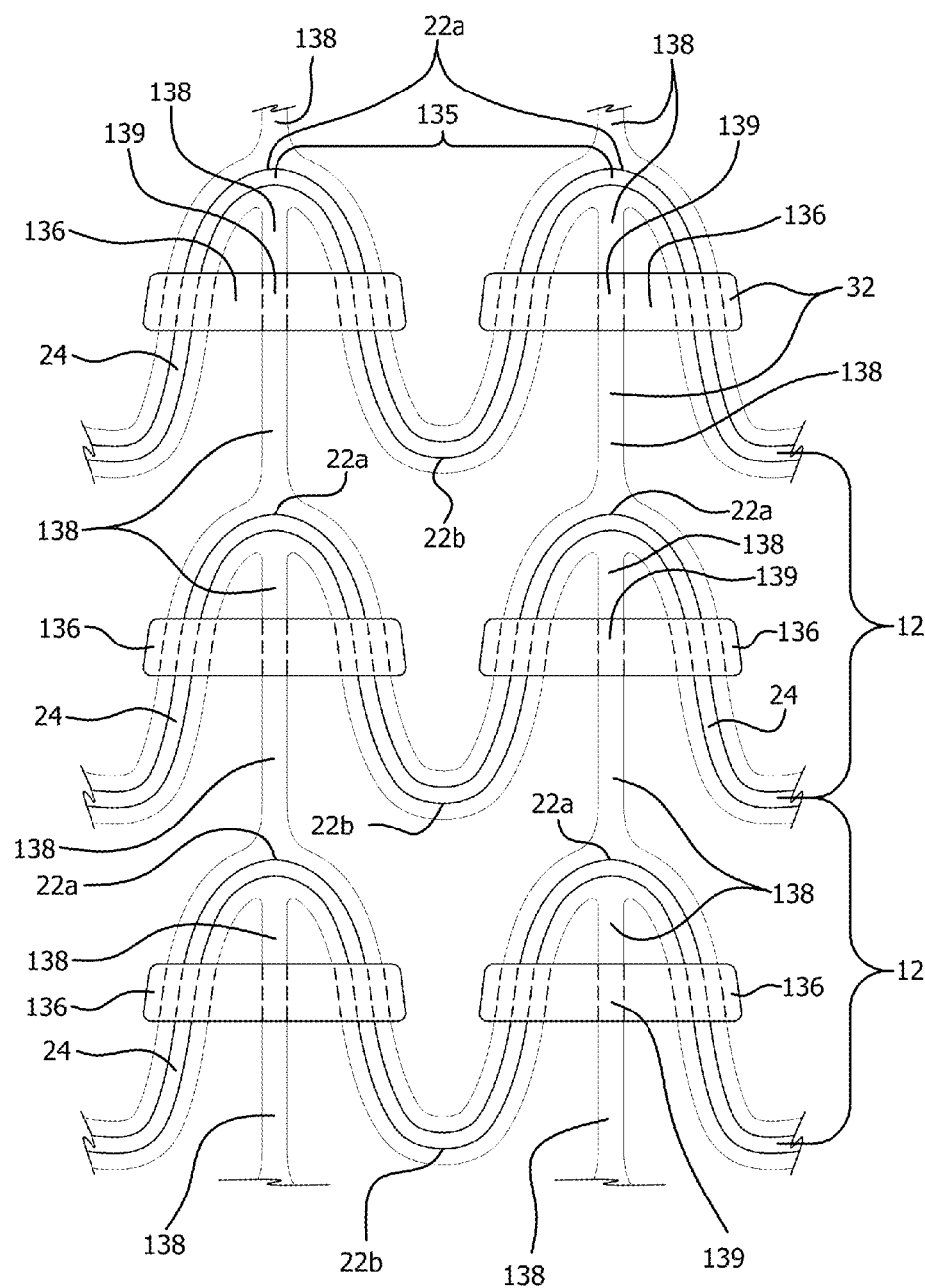
Figure 11F:
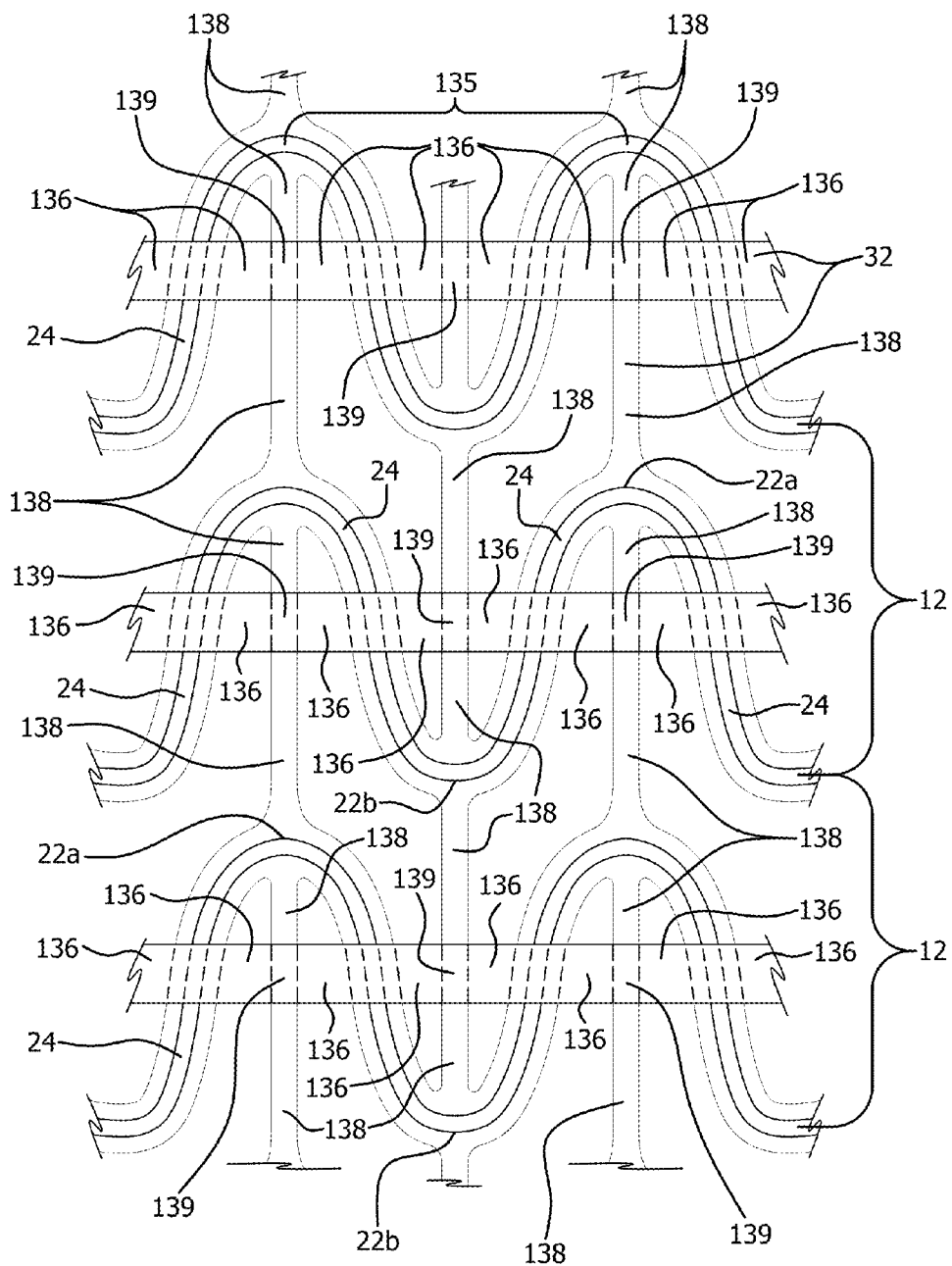

In various embodiments, a polymer web may have an elastic and a non-elastic portion. For example, as shown in FIG. 11D, the polymer web 32 has an elastic portion 136 and a non-elastic portion 138. In this embodiment, the web 32 connects between an apex of one winding to portions of the stent on either side of an apex on an adjacent winding. The elastic portion 136 is oriented such that the elasticity or stretch is oriented in a circumferential direction, i.e. a circumferential component, and the non-elastic portion 138 is oriented in a longitudinal direction, i.e. a longitudinal component. The elastic portion 136 and non-elastic portion 138 overlap each other at an attachment zone 139. The non-elastic portion 138 may extend in a longitudinal direction to connect an apex 22a from one stent element 12 to an apex 22a on an adjacent stent element 12 as shown in FIG. 11E. Alternatively and/or additionally, the non-elastic portion 138 may extend in a longitudinal direction to connect an apex 22b from one stent element 12 to an apex 22b on an adjacent stent element 12 as shown in FIG. 11F. The elastic portion 136 may alternatively or additionally connect circumferentially adjacent apices 22b or 22a as compared to connecting circumferentially adjacent wire straight segments 24. In some cases there may be multiple longitudinal components connecting longitudinally adjacent stent elements 12 between circumferentially adjacent stent elements 135. In some cases it may be desired to have the circumferential component non-elastic and the longitudinal component elastic or a combination thereof.

The elastic portion 136 can alternatively be oriented at an angle such that it is partially oriented in the longitudinal direction and partially oriented in the circumferential direction. The elastic portion 136 and non-elastic portion 138 intersect and are attached in an attachment zone 139 as shown in FIGS. 11D, 11E and 11F. A web with an elastic portion 136 and a non-elastic portion 138 may be useful when trying to minimize folding of the web into the luminal space but still maintain longitudinal strength. The elastic portion 136 may retract without substantially folding when constrained circumferentially so there is minimal to no folding within the luminal space, and the non-elastic portion 138 is oriented longitudinally through the apices 22a and provides longitudinal strength and because of its narrower width, when the stent is compacted circumferentially for example, the elastic portion does not substantially fold along its length. The non-elastic portion 138 and the elastic portion 136 may have a $M_r/M_p>0.2$.

One method of producing a polymer web 32 with the elastic portion 136 and the non-elastic portion 138 (as generally shown by FIGS. 11D-11F) is as follows. With provided stent as described herein, wrap non elastic film on entire stent as also previously described, and then selectively remove the non-elastic film, with a laser, for example, as described previously, such that the only non-elastic material left is as shown by the non-elastic portion 138. The non-elastic portion 138 may span the entire space between two longitudinally adjacent 22a apices of adjacent stent elements 12. The non-elastic film can also cover the wire 18 or it can not cover the wire 18 in the straight segments 24 of the stent frame.

The film can be heat retracted at this point in the process before the elastic film is applied. Next, if needed, wrap a layer of adhesive where the elastic portion is to be wrapped. The elastic film can be stretched up to the end of its elastic zone, such that if the film was released it would rebound back to its prestretched condition, and wrapped onto the stent in this stretched or a partially stretched state. The film can be wrapped in a helical direction or a circumferential direction ensuring that an attachment zone 139 is created at the overlap of the elastic portion 136 and the non-elastic portion 138 exists. If desired, then trim the elastic portion 136 where needed. Then heat treat the stent with the elastic and non-elastic material at a temperature sufficient to make the adhesive flow and adhere. If FEP is used, heat treat at approximately 270 C. Since the material is elastic, the elastic portion 136 may extend circumferentially between circumferentially adjacent windings 135. The elastic portion may connect the wire straight segments 24 between circumferentially adjacent windings 135. The elastic portion 136 can aid in circumferential strength and stability.

Figure 12:
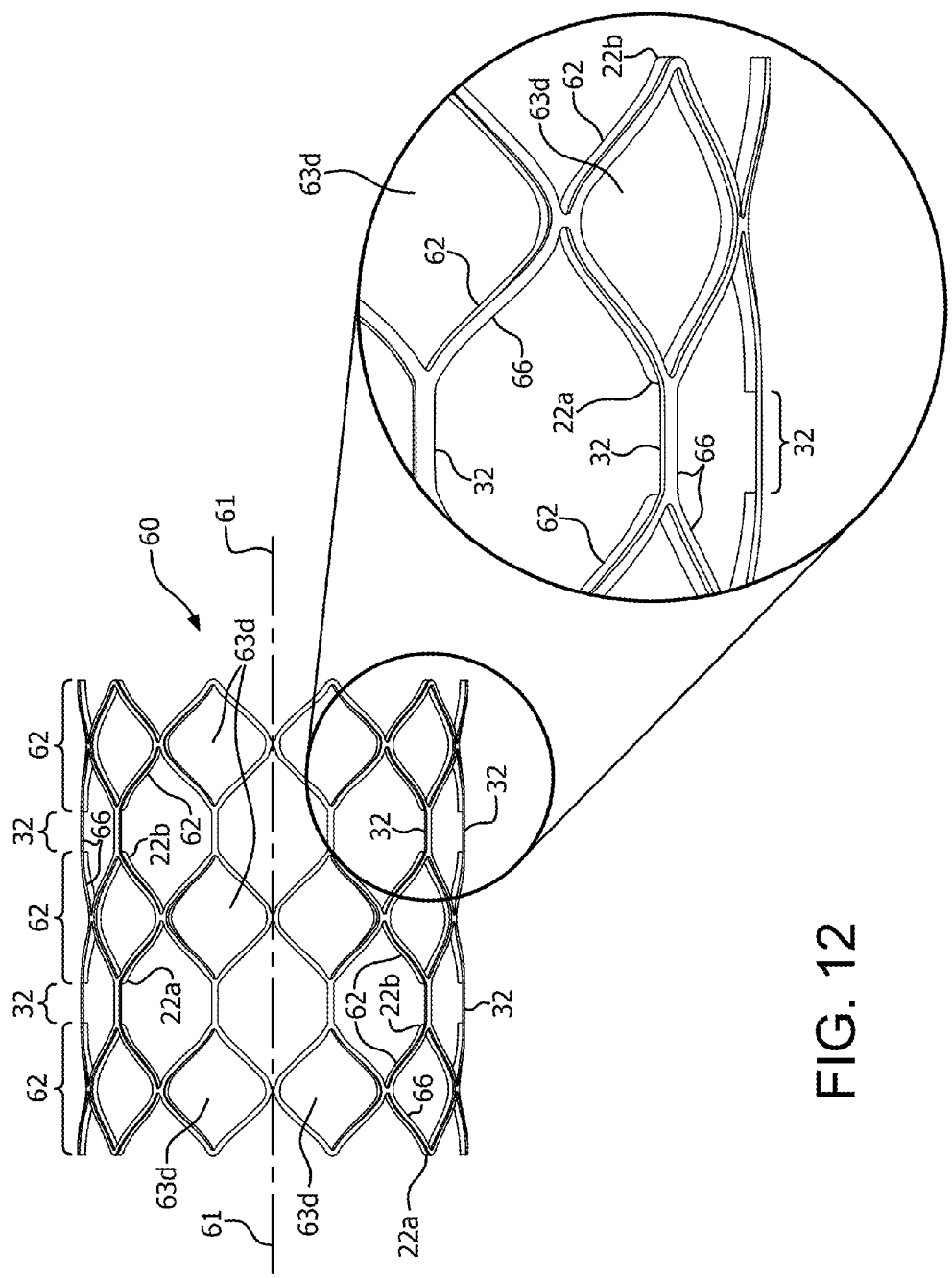
FIG. 12 is a side perspective view of a balloon expandable stent (or a length portion of such a stent) provided with flexible interconnecting webs between adjacent stent elements.

FIG. 12 shows a perspective view of a balloon expandable stent 60, as it appears following diametrical expansion with a balloon. The stent 60 shown comprises rings 62 wherein the balloon-expanded stent elements form multiple diamond-shaped openings 63d; stent 60 is typically comprised of one or more of these rings 62. The individual rings 62 may be constructed by any suitable means known in art but can be fabricated from a laser cut tube. For clarity, only the side of the tubular stent 60 closest to the viewer is shown. Stent 60 is provided with a polymeric covering 66, preferably of a flexible film. It is apparent how covering 66 interconnects the multiple rings 62 to create stent 60, via webs 32 that span the distance between apices 22a and 22b of adjacent rings 62. The webs 32 have a $M_r/M_p$ ratio greater than 0.2.

While various polymeric films may be suitable for use as the stent covering (or coating) material for this device, combinations of FEP (fluorinated ethylene propylene) films used in combination with ePTFE films are an example of one combination. In one embodiment, an ePTFE film for this device is a uni-axial film having higher strength in one direction, with the direction primarily aligned with the longitudinal axis 61 of the stent prior to balloon expansion. This type of film is similar to that described in U.S. Pat. No. 5,476,589. In another embodiment, the film can be modified with an application of a discontinuous coating of FEP similar to that taught in U.S. Pat. No. 6,159,565. As already mentioned, films may be of an elastic material such that when the linkages are formed, the linkages can stretch and return back to the pre-stretched state. These linkages can be formed before any heat retraction process is completed.

Figure 13:
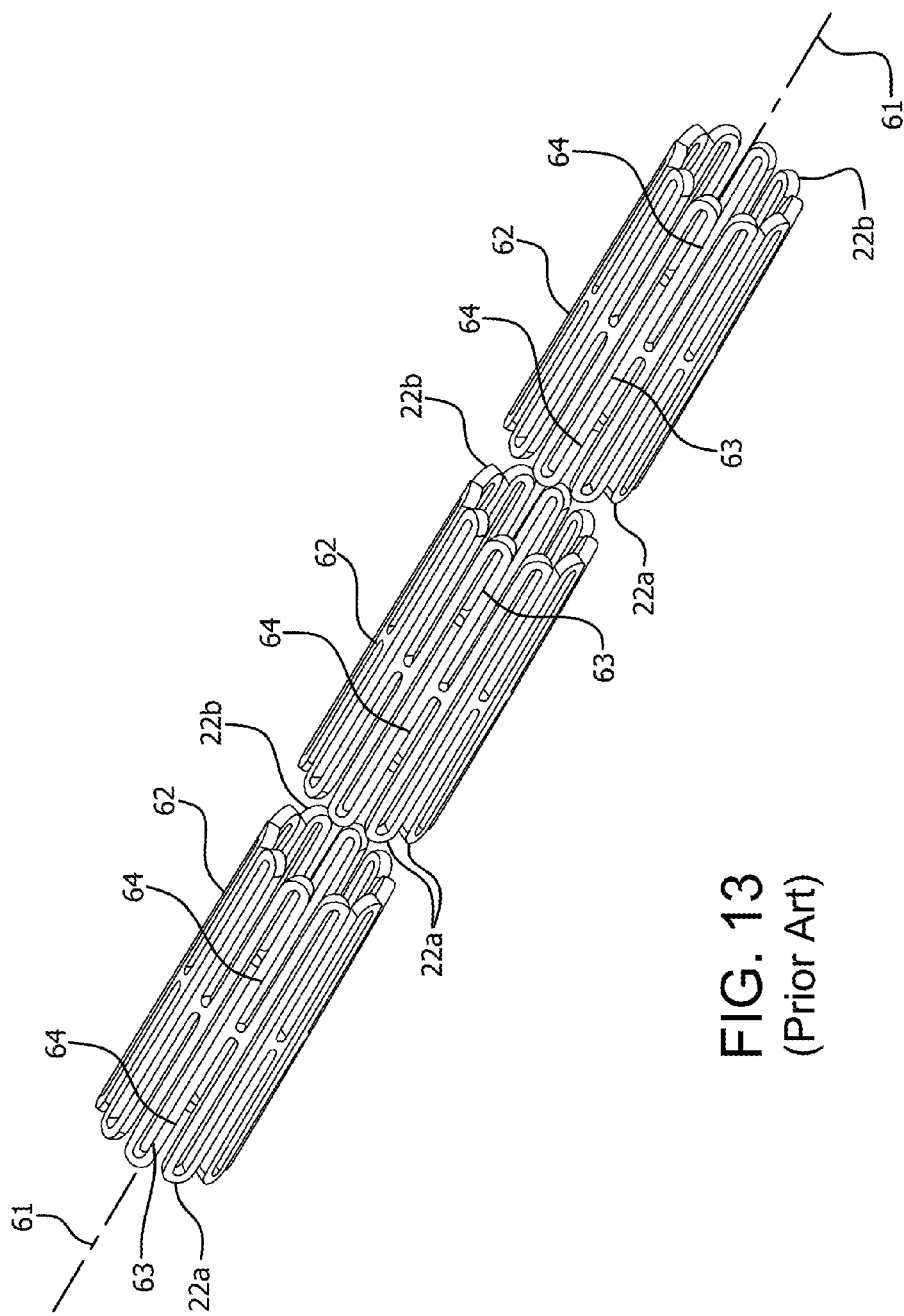
FIG. 13 is a side perspective view of previously known art where three stent rings are shown without an interconnecting polymeric covering.

The arrangement of stent rings 62 are shown in FIG. 13 without polymeric covering 66 as the rings 62 would appear prior to balloon expansion. Unexpanded stent rings 62 are cut to have openings 63 which become diamond shaped openings 63d when expanded (as shown in FIG. 12). Stent rings 62 are placed in proximity to one another with apices 22a and 22b in a typical apex to apex alignment. It is apparent that the distance between adjacent rings 62 may be as desired.

Figure 14:
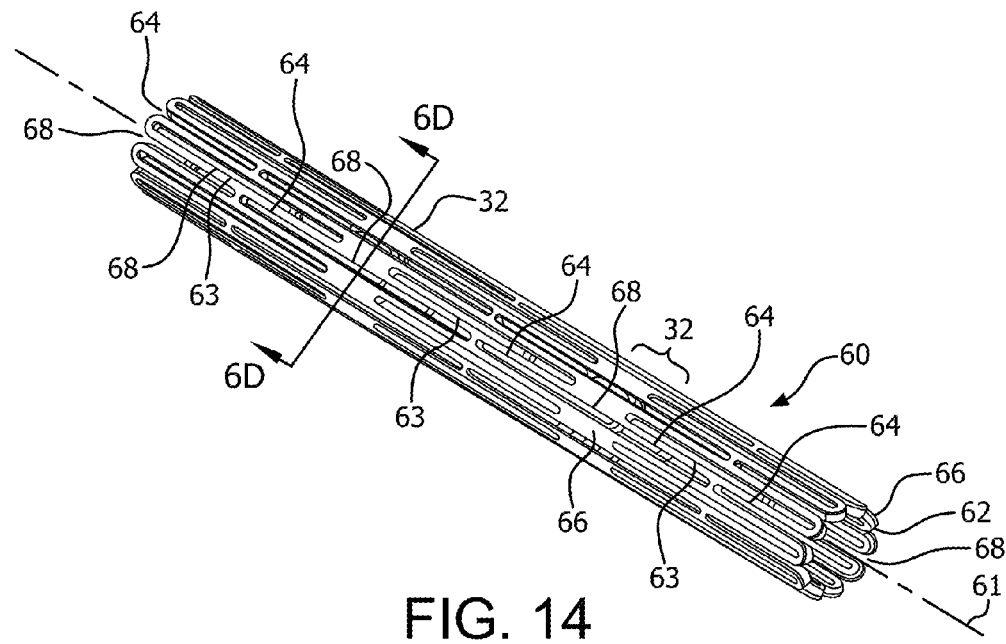
FIG. 14 is a side perspective view of a stent assembly, comprising the stent rings shown in FIG. 13, provided with an interconnecting polymeric covering
Figure 15:
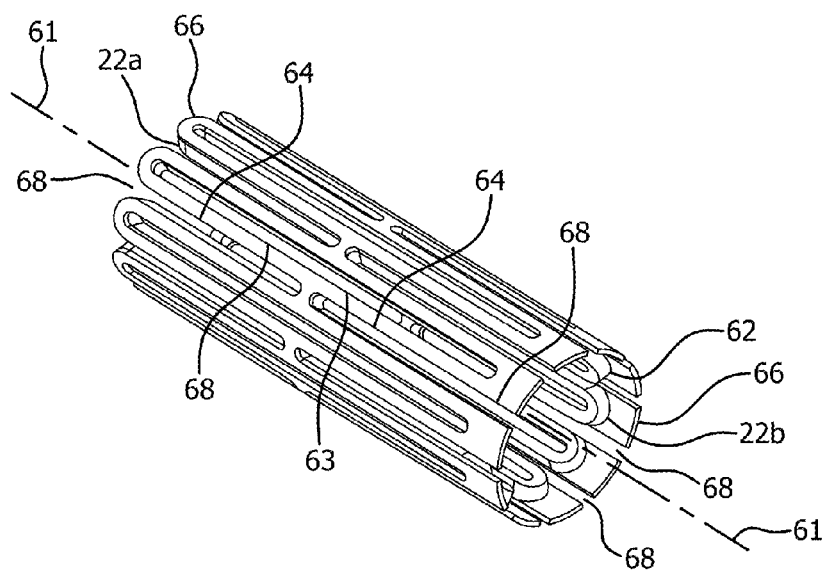
FIG. 15 is the upper left section of the stent assembly described by FIG. 14, shown as a perspective detail.

FIG. 14 illustrates the stent rings 62 as shown previously in FIG. 13 with the addition of interconnecting polymeric covering 66. Webs 32, each a portion of polymeric covering 66, are shown to interconnect adjacent rings 62. FIG. 15 is an enlarged detail perspective view of the upper left end of stent 60 described in FIG. 14.

In various embodiments, punctures or slits 68 can be formed into a covering 66. For example, as shown in FIGS. 14 and 15 the punctures or slits 68 are arranged in the polymeric covering 66 along a longitudinal axis 61 of stent 60. FIGS. 13-15 show a multiplicity of openings 63 and 64 formed between adjacent stent elements of stent rings 62. Slits or apertures 68 sized such as previously described through polymeric covering 66 are formed of size and shape such that webs 32 have a $M_r/M_p>0.2$. These slits or apertures 68 may be formed by various means as previously described and the slits may go through the film thickness or they may create pockets by only going partially through the thickness of the film. Slits 68 are formed through the polymeric covering 66 that covers openings 63 that extend between opposing apices 22a and 22b (openings that are enclosed between the ends of each stent ring 62). Alternate openings 64 that extend from the middle of the length of each stent ring 62 and fully to the end of each stent ring 62 (i.e. between radially adjacent apices 22a and 22a, and likewise between radially adjacent apices 22b and 22b) are also provided with slits through the covering polymeric material 66. These slits 68 extend longitudinally between adjacent rings 62 and into the corresponding opening in the adjacent ring 62. These slits 68 collectively create individual interconnecting webs 32. Slits 68 may be of width as desired; the width of a scalpel blade may be deemed sufficient even though the figures show that width of slit 68 corresponding to the width of the underlying stent openings 63 and 64.

Figure 16:
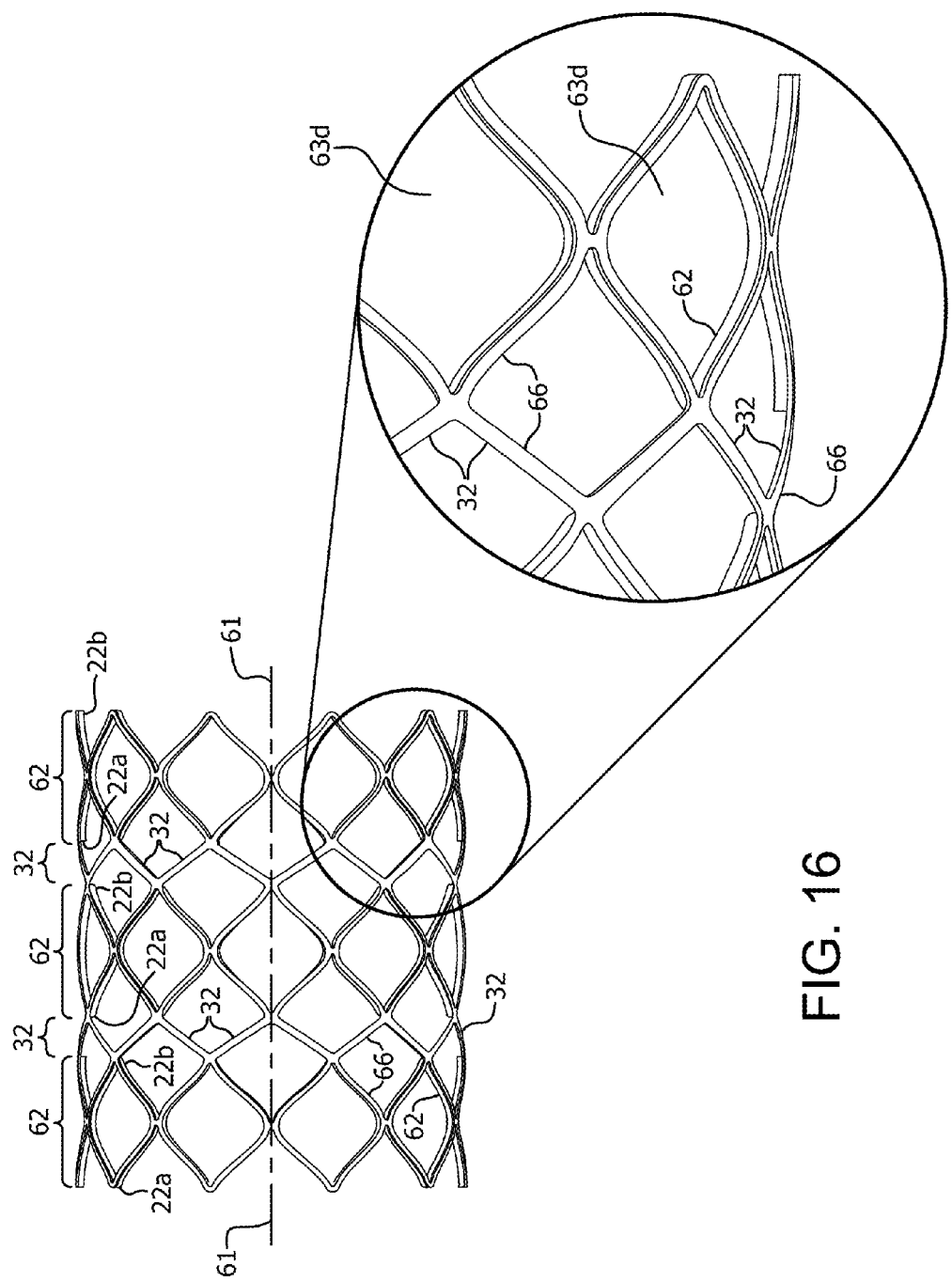
FIG. 16 is a side perspective view of a balloon expandable stent (or a length portion of such a stent) provided with flexible interconnecting webs between adjacent stent elements.

The apices 22a and 22b of each ring 62 may be made to point toward one another as shown in FIG. 12 or may be arranged to be offset as shown in FIG. 16 (i.e. aligned peak-to-valley as shown in FIG. 16 as opposed to being aligned in peak-to-peak fashion as shown in FIGS. 1A through 2E, FIG. 5 and FIG. 12). The apices typically "point" in directions that are substantially parallel to the longitudinal axis 61 of the tubular form of the stent 60.

One method of making a stent such as a stent shown in FIGS. 12 through 16 is as follows. Standard diamond pattern geometry stents can be laser machined and electro-polished at Laserage Technology Inc, Waukegan, Ill. from a 316 LVM stainless steel tube measuring 4.19 mm diameter times.0.38 mm wall thickness. The stent then is exposed to a surface roughening step to improve adherence without degrading fatigue durability performance. Plasma treatment of the stents performed prior to FEP powder coating for purposes of cleaning and reducing contact angle of the metal surface is beneficial. Plasma treatment performed as commonly known in the arts is acceptable.

FEP powder (Daikin America, Orangeburg N.Y.) can be applied to the stent component by first stirring the powder into an airborne "cloud" in a standard kitchen-type blender and suspending the frame in the cloud until a uniform layer of powder was attached to the stent frame. The stent component then can be subjected to a thermal treatment of 320 degree C. for approximately three minutes. This causes the powder to melt and adhere as a coating over the stent component. Each ring then can be coated a second time while suspending it from the opposite end and placed in 320.degree. C. oven for 3 minutes then removed and allowed to cool to room temperature.

Seventeen layers of a thin ePTFE film provided with a discontinuous coating of FEP as previously described can be wrapped around a stainless steel mandrel measuring approximately 3.43 mm. The film is applied with its high strength orientation parallel to the longitudinal axis of the stent and with the FEP side facing out. Individual stent rings then are placed over the film tube and aligned. The stent rings then can be aligned apex to apex and separated evenly with a gap of about 2.5 mm between each ring to achieve an overall device length of about 40 mm. An additional seventeen layers of the same film can be applied as previously described except with the FEP side oriented down, toward the outer diameter of the stent.

The entire assembly can be wound with several layers of an ePTFE thread (Part #SO24T4, WL Gore, Elkton, Md.) to impart compressive forces to the underlying construct. The assembly can be placed in 320 degree C. oven (Grieves, Model MT1000, The Grieve Corporation, Round Lake, Ill.) for approximately 40 minutes. The stent assembly is then removed and allowed to cool to room temperature. The over-wrap is then removed and the slits are created, such that $M_r/M_p > 0.2$, and excess material can be removed.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

We claim:

1. An endoprosthesis having a length, a radius, an inner circumference and an outer circumference, the endoprosthesis comprising:
   adjacent stent elements;
   a flexible connecting element that spans across a space between adjacent stent elements; and
   wherein the flexible connecting element has a section modulus ($M_r$) in a direction aligned with the radius of the endoprosthesis and a section modulus ($M_p$) aligned in a direction perpendicular to the radius of the endoprosthesis;
   wherein $M_r/M_p > 0.2$ such that the flexible connecting element is configured to fold substantially within the inner circumference and the outer circumference of the endoprosthesis when the endoprosthesis is compacted longitudinally.

2. An endoprosthesis according to claim 1 wherein the flexible connecting element further comprises a thickness and a width and the thickness is greater than one tenth the width.

3. An endoprosthesis according to claim 1 wherein the endoprosthesis is compacted radially.

4. An endoprosthesis according to claim 1 wherein the endoprosthesis is compacted axially.

5. An endoprosthesis according to claim 1 wherein a portion of the endoprosthesis is compacted axially during bending.

6. An endoprosthesis according to claim 1 wherein there are at least two connecting elements spanning the space between longitudinally adjacent stent elements, defining at least two boundaries of an enclosed opening.

7. An endoprosthesis according to claim 6 wherein the enclosed opening has a first end and a second end opposite the first end and one of the ends has a concave shape and the other end has a convex shape.

8. An endoprosthesis according to claim 1 wherein the stent elements are made from a continuous helical winding of wire.

9. An endoprosthesis according to claim 1 wherein the flexible connecting element further comprises a length and a width, wherein the length is at least five times the flexible connecting element width.

10. An endoprosthesis according to claim 1 wherein the flexible connecting element further comprises a width and a thickness and wherein the width is less than ten times the flexible connecting element thickness.

11. An endoprosthesis according to claim 1 wherein the flexible connecting element further comprises a web extension that attaches the flexible connecting element to adjacent stent elements with a web extension length and a web extension width.

12. An endoprosthesis according to claim 11 wherein the flexible connecting element further comprises a length and wherein the web extension length is less than the flexible connecting element length.

13. An endoprosthesis according to claim 1 wherein the flexible connecting element has a varying section modulus $M_r$.

14. An endoprosthesis according to claim 1 wherein the endoprosthesis further comprises a reservoir.

15. An endoprosthesis according to claim 1, wherein the endoprosthesis has a centerline and the flexible connecting element has a centerline that defines an angle of greater than 45 degrees with respect to the centerline of the endoprosthesis and Mr/Mp ratio >0.5.

16. The endoprosthesis according to claim 1, wherein the flexible connecting element is a flexible film.

17. The endoprosthesis according to claim 1, wherein the adjacent stent elements are formed of a first material and the connecting element is formed of a second material that is different than the first material.

18. The endoprosthesis according to claim 1, wherein the adjacent stent elements are metallic and the flexible connecting element is polymeric.

19. The endoprosthesis according to claim 1, wherein the flexible connecting element has a width less than 20 times the thickness.

20. An endoprosthesis having a length, a radius, an inner circumference, and an outer circumference, the endoprosthesis comprising:
    a first stent element having multiple apices;
    a second stent element adjacent to the first stent element and having multiple apices; and
    at least two flexible connecting elements that attach an apex of the first stent element to two apices of the second stent element across a space between the first and second stent elements;
    wherein the flexible connecting elements have a section modulus ($M_r$) in a direction aligned with the radius of the endoprosthesis and a section modulus ($M_p$) aligned in a direction perpendicular to the radius of the endoprosthesis; and
    wherein $M_r/M_p > 0.2$ such that the at least two flexible connecting elements fold substantially in plane from an expanded configuration in which the at least two flexible connecting elements extend substantially entirely within the inner circumference and the outer circumference of the endoprosthesis to a compacted configuration in which the at least two flexible connecting elements extend substantially entirely within the inner circumference and the outer circumference of the endoprosthesis when the endoprosthesis is compacted longitudinally.

21. An endoprosthesis according to claim 20 wherein $M_r/M_p > 0.4$.

22. An endoprosthesis according to claim 20 wherein the flexible connecting element is at an angle greater than 15 degrees and less than 75 degrees.

23. An endoprosthesis according to claim 20 wherein the flexible connecting element comprises an elastic material.

24. An endoprosthesis according to claim 20 wherein the flexible connecting element further comprises a web extension that attaches the flexible connecting element to adjacent first and second stent elements.

25. An endoprosthesis according to claim 20 wherein the flexible connecting element has a varying section modulus $M_r$.

26. An endoprosthesis according to claim 20 wherein the endoprosthesis further comprises a reservoir.

27. An endoprosthesis according to claim 26 wherein the reservoir has a covering.

28. An endoprosthesis having a length, a radius, and a circumference, the endoprosthesis comprising;
    a first stent element with multiple apices;
    a second stent element adjacent to the first stent element and having multiple apices;
    at least two flexible connecting elements that attach an apex of the first stent element to two apices of the second stent element across a space between the first and second stent elements, wherein each of the flexible connecting elements has a section modulus ($M_r$) in a direction aliened with the radius of the endoprosthesis and a section modulus ($M_p$) aligned in a direction erendicular to the radius of the endoprosthesis:
    wherein $M_r/M_p > 0.2$ such that the each of the flexible connecting elements is configured to fold substantially within the inner circumference and the outer circumference of the endoprosthesis when the endoprosthesis is compacted longitudinally;
    wherein the flexible connecting elements form a partial boundary to an opening; and
    wherein the opening has a first end defining a concave shape section and a second end opposite the first end, the second end defining a convex shape section, and the opening has five concave shaped sections.

29. An endoprosthesis according to 28, wherein the opening has an arrowhead shape.

30. An endoprosthesis according to 28, wherein the opening further comprises 4 straight edges.

31. An endoprosthesis according to claim 28,
    wherein the flexible connecting elements have a cross section that is non-rectangular.

32. An endoprosthesis according to 31, wherein the cross section is triangular shaped.

33. An endoprosthesis according to 31, wherein the cross section has more than four edges.

34. An endoprosthesis according to claim 28,
    wherein the flexible connecting element has an elastic portion and a non-elastic portion.

35. An endoprosthesis according to claim 34, wherein the elastic portion is oriented in a circumferential direction.

36. An endoprosthesis according to claim 34 wherein the non-elastic portion is oriented in a longitudinal direction.

37. An endoprosthesis according to claim 28,
    wherein the flexible connecting elements have a web reinforcement.

38. An endoprosthesis according to claim 28, wherein
at least one of the flexible connecting elements
has two edges and
one edge has two convex shapes and one concave shape and the opposite edge has two concave shapes and one convex shape.

* * * * *